(12) United States Patent
Peters et al.

(10) Patent No.: US 7,833,748 B1
(45) Date of Patent: Nov. 16, 2010

(54) IDENTIFICATION OF SYN-STEMODENE SYNTHASE

(75) Inventors: Reuben J. Peters, Ames, IA (US); Meimei Xu, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 508 days.

(21) Appl. No.: 11/866,525

(22) Filed: Oct. 3, 2007

Related U.S. Application Data

(60) Provisional application No. 60/827,935, filed on Oct. 3, 2006.

(51) Int. Cl.
*C12N 15/29* (2006.01)
*C12N 15/52* (2006.01)

(52) U.S. Cl. .................. 435/41; 536/23.2; 536/23.6

(58) Field of Classification Search .............. None
See application file for complete search history.

(56) References Cited

OTHER PUBLICATIONS

Kanno Y. et al. Biosci, Bioteachnol. Biochem. 2006, vol. 70, No. 7; pp. 1702-1710.*

Cho et al., "Molecular cloning and characterization of a cDNA encoding ent-cassa-12,15-diene synthase, a putative diterpenoid phytoalexin biosynthetic enzyme, from suspension-cultured rice cells treated with a chitin elicitor", The Plant Journal, 37:1-3 (2004).

Morrone, Dana et al., "An unexpected diterpene cyclase from rice: Functional identification of a stemodene synthase", Carchives of Biochemistry and Biophysics 448 (2006) 133-140.

Nemoto et al., "Stemar-13-3n3 synthase, a diterpene cyclase involved in the biosynthesis of the phytoalexin oryzalexin S in rice", FEBS Letters 571:182-186 (2004).

Otomo et al., "Diterpene Cyclases Responsible for the Biosynthesis of Phytoalexins, Momilactones A, B, and Oryzalexins A-F in Rice", Biosci. Biotechnol. Biochem. 68(9):2001-2006 (2004).

Otomo et al., Biological functions of ent- and syn-copalyl diphosphate synthases in rice: key enzymes for the branch point of gibberellin and phytoalexin biosynthesis, The Plant Journal (2004) vol. 39, pp. 886-893.

Prisic et al., "Rice Contains Two Disparate ent-Copalyl Diphosphate Synthases with Distinct Metabolic Functions", Plant Physiology, vol. 136:4228-4236 (2004).

Sakamoto et al., "An Overview of Gibberellin Metabolism Enzyme Genes and Their Related Mutants in Rice", Plant Physiology, vol. 134:1642-1653 (2004).

Wilderman et al., "Identification of Syn-Pimara-7,15-Diene Synthase Reveals Functional Clustering of Terpene Synthases Involved in Rice Phytoalexin/Allelochemical Biosynthesis", Plant Physiology, 135:2098-2105 (2004).

Xu, Meimei et al., "Functional characterization of the rice kaurene synthasae-like gene family", Phytochemistry 68 (2007) 312-326.

* cited by examiner

*Primary Examiner*—Russell Kallis
(74) *Attorney, Agent, or Firm*—McKee, Voorhees & Sease, P.L.C.

(57) ABSTRACT

The present invention relates to the isolation, purification, sequencing, and functional characterization of the class I diterpene synthase sequence OsKSL11. Transcriptional control of OsKSL11 provides a means of regulating production of stemodene. Further, since OsKSL11 is highly homologous to OsKSL8, identification of the sequence of OsKSL11 will facilitate identification of underlying enzymatic determinants that affect product outcomes with these enzymes.

4 Claims, 4 Drawing Sheets

IDENTIFICATION OF SYN-STEMODENE SYNTHASE

CROSS-REFERENCE TO RELATED APPLICATIONS

This application claims priority to provisional application Ser. No. 60/827,935 filed Oct. 3, 2006, herein incorporated by reference in its entirety.

GRANT REFERENCE CLAUSE

This invention was made with government support under Grant No. 2005-35318-15477 awarded by USDA. The government has certain rights in this invention.

BACKGROUND OF THE INVENTION

Plants produce a vast and diverse array of low-molecular weight organic compounds. A small number of these are primary metabolites, which are common to all plant species as they are directly required for growth and development. The remaining, overwhelming majority of these natural products are considered secondary metabolites and are not found in all plants. Thus, individual species produce a limited subset of all plant natural products, although families will sometimes share common secondary metabolism (e.g., oleoresinosis in *Pinaceae*). Nevertheless, many secondary metabolites have important ecological roles, particularly in plant defense. (Croteau et al. 2000). For example, phytoalexins are produced in response to microbial infections and exhibit antimicrobial properties (VanEtten et al. 1994), while allelochemicals are secreted to the rhizosphere, and suppress germination and growth of neighboring seeds (Bais et al. 2004).

Particularly abundant in plants, as both primary and secondary metabolites, are terpenoids, which comprise the largest class of natural products and exhibit wide diversity in chemical structure and biological function (Croteau et al. 2000). Much of the structural variation within this class arises from the diverse carbon backbones formed by terpene synthases (cyclases). These divalent metal ion dependent enzymes carry out complex electrophilic cyclizations and/or rearrangements to create these diverse skeletal structures from relatively simple acyclic precursors (Davis and Croteau 2000). Notably, production of a specific backbone structure either dictates, or at least severely restricts, the metabolic fate of that particular molecule. Thus, terpenoid biosynthesis is often controlled, at least in part, by regulating terpene synthase activity [e.g. giberellin biosynthesis; (Silverstone et al. 1997)].

A substantial fraction of the known terpenoids can be classified as labdane-related diterpenoids (20 carbon). These are defined here as minimally containing the bicyclic hydrocarbon structure found in the labdane class of diterpenoids, although this core structure can be further cyclized and rearranged, as in the related/derived structural classes (e.g., kauranes, abietanes, and [iso]pimaranes). Significantly, this includes the primary metabolite gibberellin growth hormones. However, the vast majority of the more than 5,000 known labdane-related diterpenoids are secondary metabolites.

Biosynthesis of labdane-related diterpenoids is initiated by class II terpene synthases which catalyze formation of the characteristic bicyclic backbone in producing specific stereoisomers of labdadienyl/copalyl disphosphate (CPP) from the universal diterpenoid precursor, and plant primary metabolite, (E,E,E)-geranylgeranyl diphosphonate (GGPP). In addition, this core bicyclic structure is always further modified by stereoselective CPP specific class I terpene synthases (i.e. ionization of the diphosphate moiety to form one or more new carbon-carbon bonds). Thus, class II and class I terpene synthases act sequentially in catalyzing stereochemically coupled cyclization reactions to form labdane-related diterpene skeletal backbones.

Significantly, the class II protonation-initiated bicyclization reaction is fundamentally different than the diphosphate ionization initiated reactions catalyzed by the more common class I terpene synthases. Nevertheless, the class II cyclases clearly fall within the terpene synthase gene family (Bohlmann et al. 1998b). However, rather than the DDXXD metal binding motif functionally associated with class I activity (Davis and Croteau 2000), class II terpene cyclases contain a distinct DXDD motif (Sun and Kamiya 1994) which has been functionally associated with class II cyclization reactions (Peters et al. 2001).

Prototypical plant class I terpene synthases are similar in size and contain two structurally defined domains (Starks et al. 1997; Whittington et al. 2002). However, some terpene synthases, and in particular all of those involved in labdane-related diterpenoid biosynthesis, contain a large amount of additional amino terminal sequence termed the 'insertional' element [approximately 240 amino acid residues; (Peters and Croteau 2002)]. Notably, given adequate sequence information, this specific structural feature is useful for putative identification of labdane-related diterpene synthases, although it is not sufficient for even such generalized functional annotation [e.g. (Bohlmann et al. 1998a)]. Rice (*Oryza sativa*) provides a model system to investigate labdane-related diterpenoid biosynthesis, as this well characterized plant is known to produce a number of such natural products beyond the ubiquitous gibberellic acid (GA) growth hormones (FIG. 1). These compounds include momilactones A and B (Kato et al. 1973; Cartwright et al. 1981), oryzalexins A to F (Akatsuka et al. 1985; Sekido et al. 1986; Kato et al. 1993; 1994), oryzalexin S (Kodama et al. 1992), and phytocassanes A to E (Koga et al. 1995; Koga et al. 1997). All of these natural products are produced in leaves in response to infection with the blast pathogenic fungus *Magneportha grisea* and exhibit antimicrobial properties; thus qualifying as phytoalexins (VanEtten et al. 1994). In addition, momilactones A and B also act as allelochemicals, as these were originally identified as dormancy factors from rice seed husks (Kato et al. 1973), and momilactone B has recently been shown to be constitutively secreted from the roots of rice seedlings, where it acts as an allelopathic agent (Kato-Noguchi and Ino 2003). Further, secretion of antimicrobial agents to the rhizosphere may also provide a competitive advantage for root establishment through local suppression of soil micro-organisms (Bais et al. 2004).

Conveniently, rice leaves produce all of these secondary metabolites after UV irradiation as well as blast fungal infection (Kodama et al. 1988), providing a standard method for inducing biosynthesis of these natural products and, presumably, transcription of the corresponding enzymatic machinery. In particular, it has previously been shown that UV irradiation induces biosynthesis of ent-sandaracopimaradiene, syn-pimara-7,15-diene, and syn-stemar-13-ene, the putative precursors to oryzalexins A to F, momilactones A and B, and oryzalexin S, respectively (Wickham and West 1992). These polycyclic diterpene hydrocarbons further have been demonstrated to be selectively produced via CPP of the corresponding stereochemistry [i.e. ent or syn; (Mohan et al. 1996)]. More recent work has identified the class I diterpene synthase producing ent-cassa-12,15-diene, the putative precursor to phytocassanes A to E (Yajima et al. 2004), stereoselectively from ent-CPP (Cho et al. 2004). In addition, it was also recently reported that only a single CPP synthase gene (OsCPS1) is involved in GA biosynthesis, although no sequence information was presented (Sakamoto et al. 2004). Thus, gene function was demonstrated by the severe growth defect (i.e. dwarf phenotype) of the corresponding mutant (i.e. T-DNA insertion) plant, along with its rescue by exogenous application of $GA_3$. Finally, although other putative class II and class I labdane-related diterpene synthase genes can be found in the rice genome, gene isolation and biochemical characterization have not been previously reported, leaving in question the role and specific activity of these additional cyclases.

The present inventors recently identified and isolated nucleic acid fragments encoding class II terpene synthases, as set forth in U.S. Ser. No. 11/135,267, the disclosure of which is hereby expressly incorporated herein by reference. This technology has provided methods of modulating terpenoid biosynthesis and expression of class II terpene synthases, including expression of a syn-copalyl disphosphate. The class I genes have been designated as OsKS1-10, although only OsKS1 actually operates in gibberellin biosynthesis and, presumably, produces ent-cassa-12,15-diene, syn-pimara-7,15 diene, and syn-stemar-13-ene have also been termed OsDTC1, OsDTS2, and OsDTC2, respectively. The inventors have now suggested the use of OsKSL (rice kaurene synthaselike), with the corresponding number from Sakamoto et al. (2004) where appropriate, for these non-kaurene producing class I genes. Thus, OsKS1 presumably produced ent-kaurene, while OsKSL4 (OsDTS2) produces syn-pimaradiene, OsKSL7 (OsDTC1) ent-cassadiene, OsKSL8 (OsDTC2) syn-stemarene, and OsKSL10 ent-sandaracopimaradiene.

The present inventors have now cloned a novel stemodene synthase member of the described family that has hereby been designated OsKSL11.

It is therefore a primary objective of the present invention to provide a novel diterpene synthase.

It is a further objective of the present invention to provide a novel diterpene synthase designated as OsKSL11.

It is a further objective of the present invention to provide a method for investigating enzymatic determinants for differential product outcome.

It is still a further objective of the present invention to provide a possible means of producing stemodanes by rice.

The method and means of accomplishing each of the above objectives as well as others will become apparent from the detailed description of the invention which follows hereafter.

SUMMARY OF THE INVENTION

The present invention relates to the functional identification of a novel class I diterpene synthase, OsKSL11, that is not present in either the genome or extensive cDNA sequence data available for rice. OsKSL11 is a syn-CPP specific exostemodene synthase. Rice has not previously been demonstrated to produce stemodene or any derived natural products. It is, however, possible that stemodante diterpenoids are produced in tissues and/or in response to other conditions, such as viral infection.

In accordance with this invention, OsKSL11 has been identified, sequenced, isolated, and biochemically characterized. The isolation and functional identification of this diterpene synthase, which is highly homologous to OsKSL8, provides a means of increasing the utility of the rice class I diterpene synthase family for examining enzymatic specificity.

DETAILED DESCRIPTION OF THE INVENTION

Figure 1:
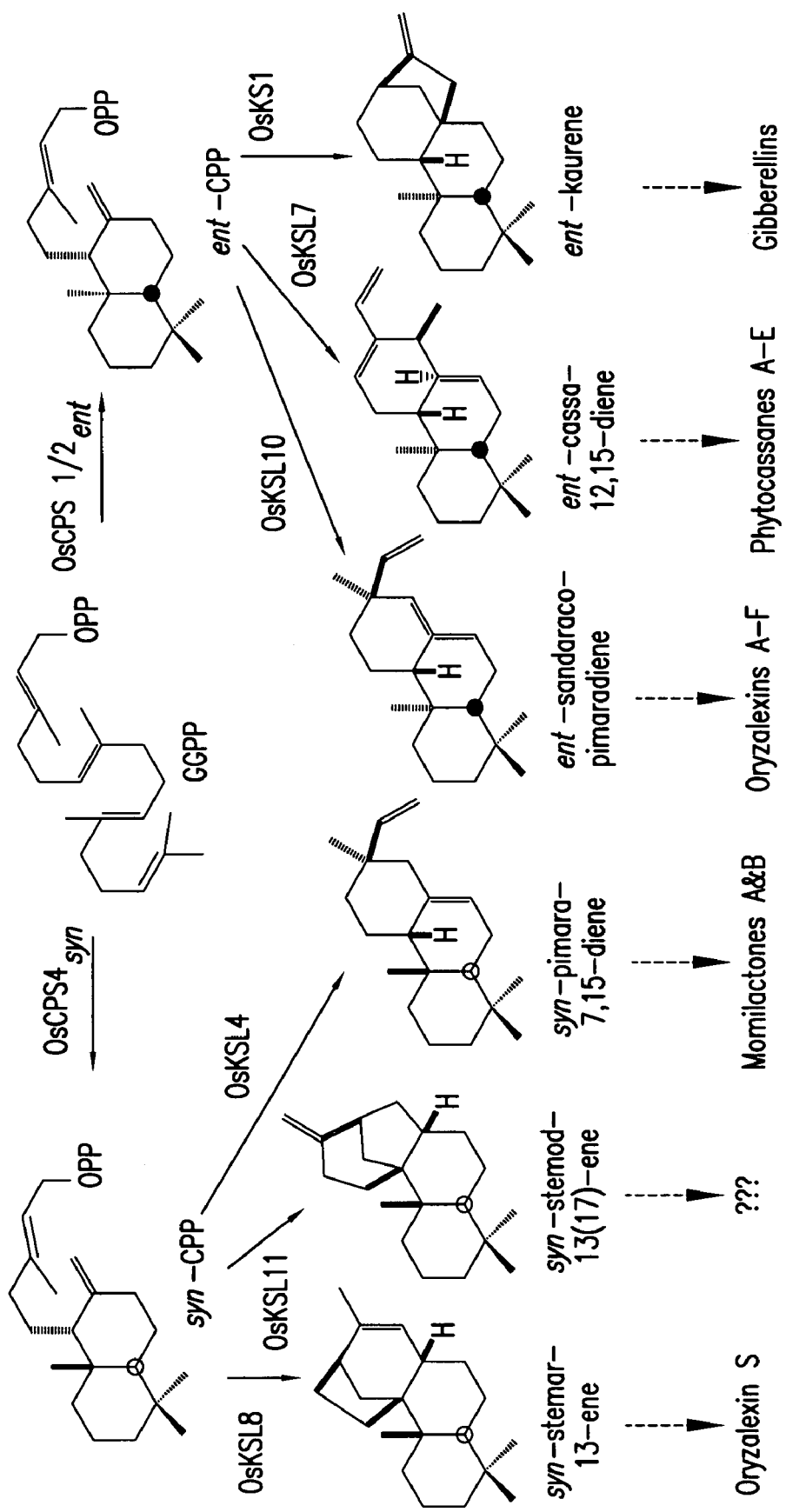
FIG. 1 shows the known cyclization steps in rice labdanerelated diterpenoid biosynthesis. Reactions catalyzed by class II (tpsII) or class I (tpsI) terpene synthases are indicated, along with the families of natural products derived from each of the named polycyclic hydrocarbon structures (dashed arrows indicate multiple enzymatic steps).

The present invention describes the class I diterpene synthase OsKSL11 that is not present in either the genome or extensive cDNA sequence data available for rice. Nevertheless, OsKSL11 clearly falls within the rice kaurene synthaselike family.

Functional characterization of OsKSL11 has demonstrated that it is a syn-CPP specific exo-stemodene synthase. Rice has not previously been demonstrated to produce stemodene or any derived natural products despite intensive phytochemical investigations. However, these studies have been almost been exclusively targeted at identification of leaf phytoalexins, and it is possible that stemodane diterpenoids are produced in other tissues and/or in response to other conditions, such as viral rather than microbial infection. Interestingly, the stemodane and stemarene diterpene skeletal types were both first defined as natural products from *Stemodia maritime*, a medicinal plant used in traditional Caribbean medicine to treat venereal disease. Stemodin, the major diterpenoid natural product in *Stemodia*, possesses antiviral activity, which may help account for the use of this plant as an herbal medicine and, more generally, for the function of this natural product in plants. Nevertheless, nothing is known about the enzymatic genes involved in biosynthesis of the *Stemodia* diterpenoid natural products, and OsKSL11 appears to be the first identified stemodene synthase.

Formation of the stemodene and stemarene backbones can be envisioned as arising from largely overlapping cyclization mechanisms. In particular, initial cyclization of syn-CPP to an isopimarenyl intermediate that undergoes a 1,2-hydride shift from C9 to C8, followed by further cyclization to an abeo-stachanyl intermediate. Alternative ring rearrangements can then form either stemodenyl or stemarenyl intermediates that undergo deprotonation to yield the final tetracyclic diterpenes. The highly homologous OsKSL11 and OsKSL8 presumably catalyze these alternative, yet mechanistically related, cyclization reactions. Hence, structurefunction analysis of this pair of cyclases should facilitate identification of the underlying enzymatic determinants for this relatively subtle change in product outcomes. In fact, OsKSL11 and OsKSL8 seem to be the most closely related pair of rice class I diterpene synthases (89% amino acid identity). Thus, identification of OsKSL11 measurably increases the utility of the rice class I diterpene synthase family for examining enzymatic specificity.

The existence of OsKSL11 indicates that rice has the capacity to produce stemodene. However, rice has not been shown to produce stemodane type diterpenoid natural products. Nevertheless, while even latent, currently untapped potential may offer some advantage in plasticity of natural products biosynthesis, the production of stemodanes by rice cannot be ruled out. It has recently been observed that *Arabidopsis thaliana* is capable of producing a much wider range of natural products than was previously appreciated.

As used here, the term "isolated" means any class I diterpene synthase of the present invention, or any gene encoding a class I diterpene synthase, which is essentially free of other polypeptides or genes, respectively, or of other contaminants with which the class I diterpene synthase polypeptide or gene might normally be found in nature.

The invention includes a functional polypeptide, OsKSL11 and functional fragments thereof. As used herein, the term "functional polypeptide" refers to a polypeptide which possesses a biological function or activity which is identified through a defined functional assay and which is associated with a particular biologic, morphologic, or phenotypic alteration in the cell. The biological function, for example, can vary from a polypeptide fragment as small as an epitope to which an antibody molecule can bind to a large polypeptide which is capable of participating in the characteristic induction or programming of phenotypic changes within a cell. A "functional polynucleotide" denotes a polynucleotide which encodes a functional polypeptide as described herein.

Minor modifications of the primary amino acid sequences of the terpene synthases of this invention may result in proteins which have substantially equivalent activity as compared to the polypeptides described herein. Such modifications may be deliberate, as by site-directed mutagenesis, or may be spontaneous. All of the polypeptides produced by these modifications are included herein as long as the described activities of the terpene synthases are present. Further, deletion of one or more amino acids can also result in a modification of the structure of the resultant molecule without significantly altering its biological activity. This can lead to the development of a smaller active molecule which would have broader utility. For example, it is possible to remove amino or carboxy terminal amino acids which may not be required for biological activity.

The polypeptides of the invention also include conservative variations of the polypeptide sequences. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

The invention is also intended to include synthetic peptides. The amino acid sequence of SEQ ID NO: 5 (FIG. 2), and conservative variations, comprise the synthetic peptides of the invention. As used herein, the term "synthetic peptide" denotes a peptide which does not comprise an entire naturally occurring protein molecule. The peptide is "synthetic" in that it may be produced by human intervention using such techniques as chemical synthesis, recombinant genetic techniques, or fragmentation of whole antigen or the like.

Peptides of the invention can be synthesized by such commonly used methods as t-BOC or FMOC protection of alpha-amino groups. Both methods involve stepwise syntheses whereby a single amino acid is added at each step starting from the C-terminus of the peptide (See, Coligan, et al., Current Protocols in Immunology, Wiley Interscience, 1991, Unit 9). Peptides of the invention can also be synthesized by the well known solid phase peptide synthesis methods described in Merrifield, J. Am. Chem. Soc., 85:2149, 1962, and Stewart and Young, Solid Phase Peptides Synthesis, (Freeman, San Francisco, 1969, pp. 27-62), using a copoly (styrene-divinylbenzene) containing 0.1-1.0 mMol amines/g polymer. On completion of chemical synthesis, the peptides can be deprotected and cleaved from the polymer by treatment with liquid HF-10% anisole for about ¼-1 hours at 0° C. After evaporation of the reagents, the peptides are extracted from the polymer with 1% acetic acid solution which is then lyophilized to yield the crude material. This can normally be purified by such techniques as gel filtration on Sephadex G-15 using 5% acetic acid as a solvent. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy molar, rotation, solubility, and quantitated by the solid phase Edman degradation.

As used herein, "polynucleotide" refers to a polymer of deoxyribonucleotides or ribonucleotides, in the form of a separate fragment or as a component of a larger construct. As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, preferably at least 55%, preferably at least 60%, more preferably at least 70%, 80%, 90%, and most preferably at least 95%.

DNA encoding the polypeptide of the invention can be assembled from cDNA fragments or from oligonucleotides which provide a synthetic gene which is capable of being expressed in a recombinant transcriptional unit. Polynucleotide sequences of the invention include DNA, RNA and cDNA sequences. Preferably, the nucleotide sequence encoding the diterpene synthase of this invention has the sequence of SEQ ID NO: 5.

DNA sequences of the invention can be obtained by several methods. For example, the DNA can be isolated using hybridization procedures which are well known in the art. These include, but are not limited to: 1) hybridization of probes to genomic or cDNA libraries to detect shared nucleotide sequences; 2) antibody screening of expression libraries to detect shared structural features and 3) synthesis by the polymerase chain reaction (PCR).

Hybridization procedures are useful for the screening of recombinant clones by using labeled mixed synthetic oligonucleotide probes where each probe is potentially the complete complement of a specific DNA sequence in the hybridization sample which includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., Nucleic Acid Research, 9:879, 1981).

The development of specific DNA sequences encoding OsKSL11 can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA. Of these three methods for developing specific DNA sequences for use in recombinant procedures, the isolation of genomic DNA isolates is the least common.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay et al., Nucl. Acid Res. 11:2325, 1983).

A cDNA expression library, such as lambda gt 11, can be screened indirectly for polypeptides having at least one epitope, using antibodies specific for class I diterpene synthases. Such antibodies can be either polyclonally or monoclonally derived and used to detect expression product indicative of the presence of diterpene synthase cDNA.

A polynucleotide sequence can be deduced from the genetic code. However, the degeneracy of the code must be taken into account. Polynucleotides of the invention include sequences which are degenerate as a result of the genetic code. The polynucleotides of the invention include sequences that are degenerate as a result of the genetic code. There are 20 natural amino acids, most of which are specified by more than one codon. Therefore, as long as the amino acid sequences of the class II terpene synthases results in a functional polypeptide (at least, in the case of the sense polynucleotide strand), all degenerate nucleotide sequences are included in the invention.

The polynucleotide sequences for the diterpene synthases of this invention also include sequences complementary to the polynucleotide encoding these terpene synthases (antisense sequences). Antisense nucleic acids are DNA or RNA molecules that are complementary to at least a portion of a specific mRNA molecule (Weintraub, Scientific American, 262:40, 1990). The invention embraces all antisense polynucleotides capable of inhibiting production of diterpene synthase polypeptides. In the cell, the antisense nucleic acids hybridize to the corresponding mRNA, forming a double-stranded molecule. The antisense nucleic acids interfere with the translation of the mRNA since the cell will not translate an mRNA that is double-stranded. Antisense oligomers of about 15 nucleotides are preferred, since they are easily synthesized and are less likely to cause problems than larger molecules when introduced into the target terpene synthase-producing cell. The use of antisense methods to inhibit the translation of genes is well known in the art (Marcus-Sakura, Anal. Biochem., 172:289, 1988).

In addition, ribozyme nucleotide sequences for OsKSL11 are included in the invention. Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, J. Amer. Med. Assn., 260:3030, 1988). A major advantage of this approach is that, because they are sequence-specific, only mRNAs with particular sequences are inactivated.

Figure 2A:
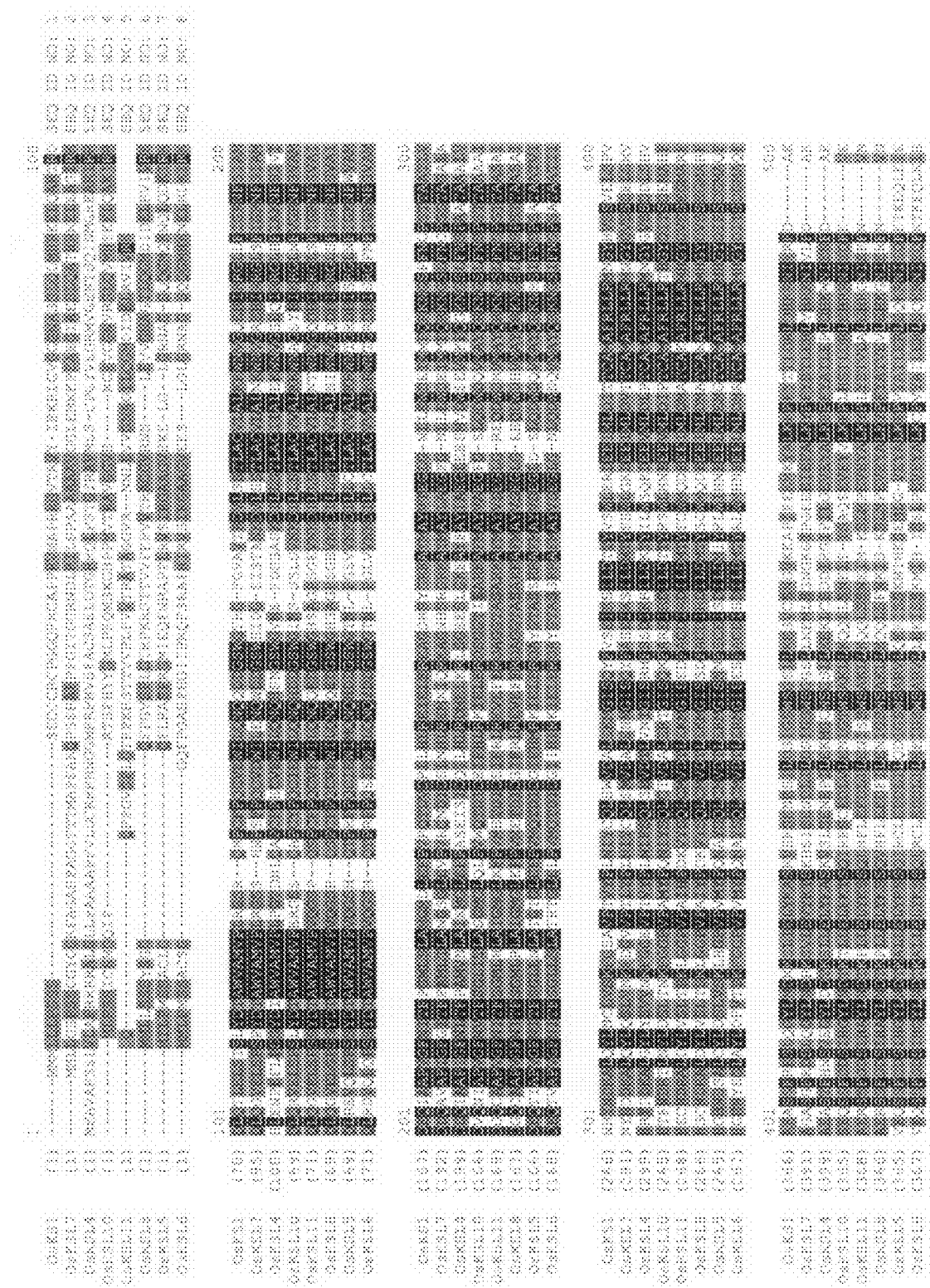
FIG. 2 shows the amino acid alignment of OSKSL11 with other functionally identified rice kaurene synthase-like enzymes: OsKS1 (SEQ ID NO: 1), OsKSL7 (SEQ ID NO: 2), OsKSL4 (SEQ ID NO: 3), OsKSL10 (SEQ ID NO: 4), OsKSL11 (SEQ ID NO: 5), OsKSL8 (SEQ ID NO: 6), OsKSL5 (SEQ ID NO: 7), and OsKSL6 (SEQ ID NO: 8). The DDXXD motif is underlined.
Figure 2B:
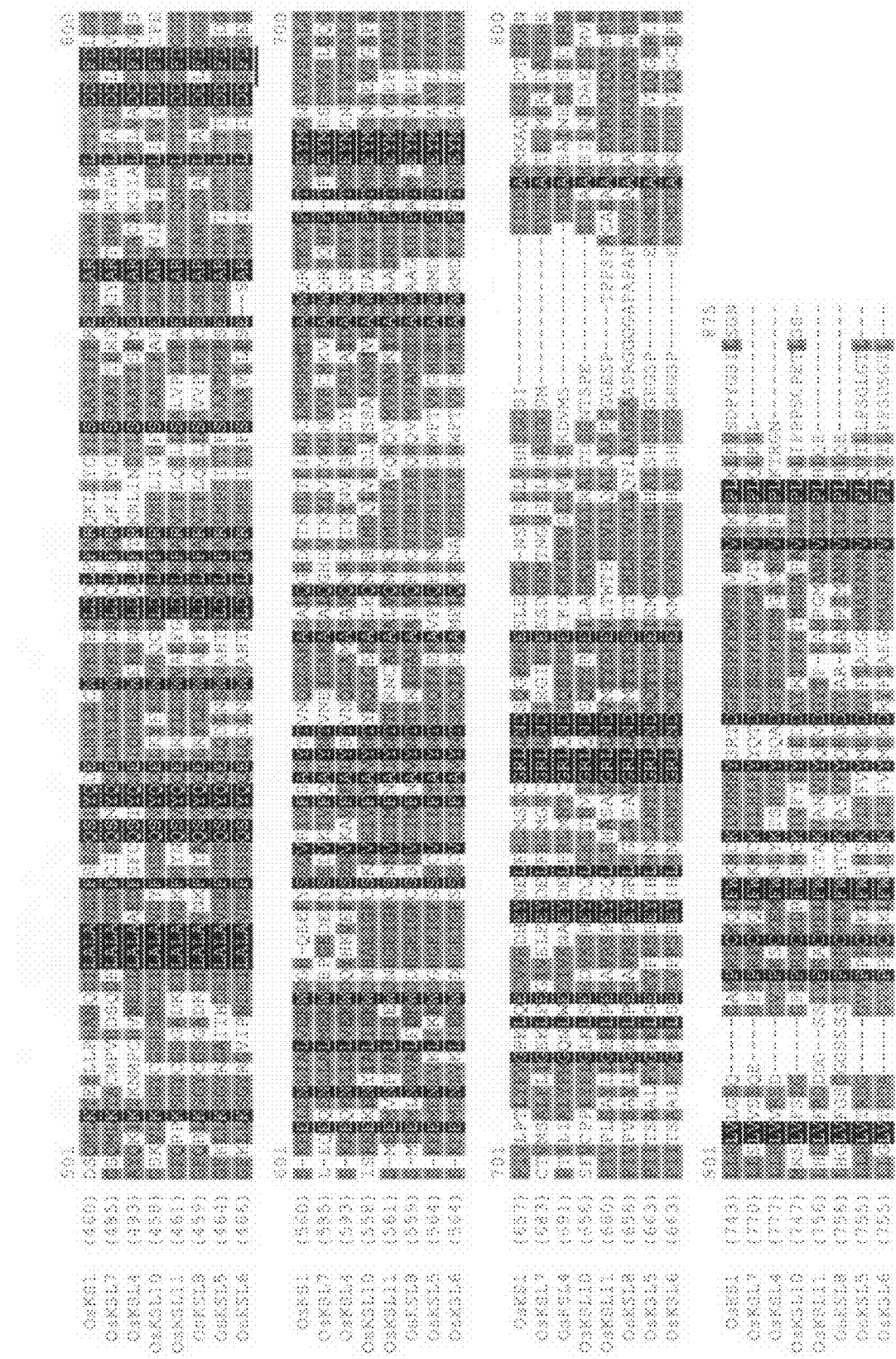

The polypeptides of the invention can also be used to produce antibodies which are immunoreactive or bind to epitopes of the terpene synthase polypeptides. Antibodies of the invention also include antibodies which bind to the synthetic peptides in SEQ ID NO: 5 (FIG. 2). Antibodies which consist essentially of pooled monoclonal antibodies with different epitopic specificities, as well as distinct monoclonal antibody preparations are provided. Monoclonal antibodies are made from antigen containing fragments of the protein by methods well known in the art (Kohler, et al., Nature, 256: 495, 1975; Current Protocols in Molecular Biology, Ausubel, et al., ed., 1989).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies which bind to the polypeptides of the invention can be prepared using an intact polypeptide or fragments containing small peptides of interest as the immunizing antigen. The polypeptides or peptides such as SEQ ID NO: 5 can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those skilled in the art will know of various techniques common in the immunology arts for purification and/or concentration of polygonal antibodies, as well as monoclonal antibodies (See for example, Coligan, et al., Unit 9, Current Protocols in Immunology, Wiley Interscience, 1991, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

Polynucleotide sequences encoding the polypeptide (SEQ ID NO: 5) of the invention can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

DNA sequences encoding the polypeptides can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, in other words when the foreign DNA is continuously maintained in the host, are known in the art.

In the present invention, the diterpene synthase polynucleotide sequences may be inserted into a recombinant expression vector. The term "recombinant expression vector" refers to a plasmid, virus or other vehicle known in the art that has been manipulated by insertion or incorporation of the genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg et al., Gene 56:125, 1987), the pMSXND expression vector for expression in mammalian cells (Lee and Nathans, J. Biol. Chem. 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

The vector may include a phenotypically selectable marker to identify host cells which contain the expression vector. Examples of markers typically used in prokaryotic expression vectors include antibiotic resistance genes for ampicillin (β-lactamases), tetracycline and chloramphenicol (chloramphenicol acetyl-transferase). Examples of such markers typically used in mammalian expression vectors include the gene for adenosine deaminase (ADA), aminoglycoside phosphotransferase (neo, G418), dihydrofolate reductase (DHFR), hygromycin-B-phosphotransferase (HPH), thymidine kinase (TK), and xanthine guanine phosphoribosyltransferse (XG-PRT, gpt).

Transformation of a host cell with recombinant DNA may be carried out by conventional techniques which are well known to those skilled in the art. Where the host is prokaryotic, such as E. coli, competent cells which are capable of DNA uptake can be prepared from cells harvested after exponential growth phase and subsequently treated by the $CaCl_2$ method by procedures well known in the art. Alternatively, $MgCl_2$ or RbC1 can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the polypeptides of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (Eukaryotic Viral Vectors, Cold Spring Harbor Laboratory, Gluzman ed., 1982). Examples of mammalian host cells include COS, BHK, 293, and CHO cells.

Isolation and purification of host cell expressed polypeptide, or fragments thereof, provided by the invention, may be carried out by conventional means including preparative chromatography and immunological separations involving monoclonal or polyclonal antibodies.

The class I diterpene synthases of the invention are useful in a screening method for identifying compounds or compositions which affect the activity of the synthases. Thus, in another embodiment, the invention provides a method for identifying a composition which affects a class I diterpene synthase of this invention comprising incubating the components, which include the composition to be tested and the synthase or a polynucleotide encoding the synthase, under conditions sufficient to allow the components to interact, then subsequently measuring the effect the composition has on synthase activity or on the polynucleotide encoding the synthase. The observed effect on the synthase may be either inhibitory or stimulatory. A polynucleotide encoding the kinase may be inserted into an expression vector and the effect of a composition on transcription of the kinase can be measured, for example, by Northern blot analysis.

Another embodiment provides a method for engineering production of syn-CPP or other molecules of the invention either ex vivo or in genetically-engineered organisms. In this respect, using the nucleic acids of the present invention, one may express a protein of the present invention in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so. It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter, such as ubiquitin, to direct transcription, a ribosome binding site for translational initiation, and a transcription/translation terminator. Constitutive promoters are classified as providing for a range of constitutive expression. Thus, some are weak constitutive promoters, and others are strong constitutive promoters. Generally, by "weak promoter" is intended a promoter that drives expression of a coding sequence at a low level. By "low level" is intended at levels of about 1/10,000 transcripts to about 1/100,000 transcripts to about 1/500,000 transcripts. Conversely, a "strong promoter" drives expression of a coding sequence at a "high level", or about 1/10 transcripts to about 1/100 transcripts to about 1/1,000 transcripts.

One of skill would recognize that modifications could be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

In another embodiment, the invention provides a method of modulating GA phytohormone and/or defensive phytoalexin biosynthesis in plants comprising administering an amount of reagent effective in modulating synthase activity. The term "effective amount" means that amount of monoclonal antibody or antisense nucleotide, for example, which is used, is of sufficient quantity to modulate terpene synthase activity.

Treatment includes administration of a reagent which modulates terpene synthase activity. The term "modulate" envisions the suppression of expression of the synthase when it is over-expressed, or augmentation of terpene synthase expression when it is under-expressed. It also envisions suppression of terpene synthase activity, for example, by using a competitive inhibitor of the natural synthase binding site in a cell. When a disorder is associated with synthase overexpression, such suppressive reagents as antisense polynucleotide sequences or binding antibodies can be introduced to a cell or plant. In addition, an anti-idiotype antibody which binds to a monoclonal antibody which binds a peptide of the invention may also be used in the therapeutic method of the invention. Alternatively, when a cell proliferative disorder is associated with underexpression or expression of a mutant polypeptide, a sense polynucleotide sequence (the DNA coding strand) or polypeptide can be introduced into the cell.

Peptides, antibodies, and polynucleotide sequences, including antisense sequences, can be therapeutically administered by various techniques known to those of skill in the art. Such therapy would achieve its therapeutic effect by introduction of the polynucleotide, into cells of plants having the proliferative disorder. Delivery of polynucleotide can be achieved using free polynucleotide or a recombinant expression vector such as a chimeric virus or a colloidal dispersion system. Especially preferred for therapeutic delivery of nucleotide sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting a terpene synthase sequence into the viral vector, along with another gene which encodes the ligand for a receptor on a specific target cell, for example, the vector is now target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsitation. Helper cell lines which have deletions of the packaging signal include but are not limited to psi2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced. The vector virions produced by this method can then be used to infect a tissue cell line, such as NIH 3T3 cells, to produce large quantities of chimeric retroviral virions.

Another targeted delivery system for polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. A preferred colloidal system of this invention is a liposome. Liposomes are artificial membrane vesicles which are useful as delivery vehicles in vitro and in vivo. It has been shown that large unilamellar vesicles (LUV), which range in size from 0.2-4.0 µm can encapsulate a substantial percentage of an aqueous buffer containing large macromolecules. RNA, DNA and intact virions can be encapsulated within the aqueous interior and be delivered to cells in a biologically active form (Fraley, et al., Trends Biochem. Sci., 6:77, 1981). In addition to plant cells, liposomes have been used for delivery of polynucleotides in animal, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., Biotechniques, 6:682, 1988).

The invention also provides a method for detecting a cell with diterpene synthase activity or a cell proliferative disorder associated with terpenoids comprising contacting a cell component with terpene synthase activity with a reagent which binds to the component and measuring the interaction of the reagent with the component. Such reagents can be used to measure relative levels of terpenoid expression compared to normal tissue. The cell component can be nucleic acid, such as DNA or RNA, or protein. When the component is nucleic acid, the reagent is a nucleic acid probe or PCR primer. The interaction of a nucleic acid reagent with a nucleic acid encoding a polypeptide with terpene synthase activity is typically measured using radioactive labels, however, other types of labels will be known to those of skill in the art. When the cell component is protein, the reagent is typically an antibody probe. The probes are directly or indirectly detectably labeled, for example, with a radioisotope, a fluorescent compound, a bioluminescent compound, a chemiluminescent compound, a metal chelator or an enzyme. Those of ordinary skill in the art will know of other suitable labels for binding to the antibody, or will be able to ascertain such, using routine experimentation.

The materials of the invention are ideally suited for the preparation of a kit. The kit is useful for the detection of the level of a diterpene synthase comprising an antibody which binds a terpene synthase or a nucleic acid probe which hybridizes to terpenoid nucleotide, the kit comprising a carrier means being compartmentalized to receive in close confinement therein one or more containers such as vials, tubes, and the like, each of the container means comprising one of the separate elements to be used in the assay. For example, one of the container means may comprise a monoclonal antibody of the invention which is, or can be, detectably labeled. The kit may also have containers containing buffer(s) and/or a container comprising a reporter-means (for example, a biotin-binding protein, such as avidin or streptavidin) bound to a reporter molecule (for example, an enzymatic or fluorescent label).

The following example is offered to illustrate but not limit the invention. Thus, they are presented with the understanding that various modifications may be made and still be within the spirit of the invention.

Example 1

Functional Identification of OsKSL11

Chemicals. The preparations of (E,E,E)-geranylgeranyl diphosphate (GGPP), and ent- and syn-copalyl diphosphate (CPP), and syn-stemarene have been previously described. (Mohan et al. 1996). Stemodene standards were derived from a 1.5:1 mixture (ca. 5 mg) of synthetic racemic exo- and endo-stemodenes, kindly provided by Jim White. (White et al. 1994). This was fractionated by flash chromatography on a silica gel column (1 cm×10 cm) using pentane and the later eluting fractions (enriched for the exo isomer) were pooled and concentrated under nitrogen to yield ~2 mg exo-stemodene (~85% purity by GC analysis). Unless otherwise noted, chemicals were purchased from Fisher Scientific (Loughborough, Leicestershire, UK) and molecular biology reagents from Invitrogen (Carlsbad, Calif., USA).

Plant material. Rice plants (Oryza sativa L. ssp. indica cv. IR24) and seedlings (ssp. japonica cv Nipponbare) were those previously described. (Xu et al. 2004). Detached leaves from 4-week-old greenhouse grown plants were UV-irradiated (254 nm from 15-cm distance for 25 min.) and then incubated for 24 h under dark, humid conditions at 30° C. Seedlings were germinated from surface sterilized seeds on filter paper in sterile 1.2% agar plates at 30° C. in the dark for a week, then sprayed with approximately 2 mL 0.1% Tween 20 with 0.5 mM methyl jasmonate per gram of plant weight, and incubated 24 h under the same conditions. The resulting tissues were frozen in liquid nitrogen and total RNA extracted using Concert Plant RNA Reagent, following the manufacturer's instructions.

Cloning. Using the predicted sequence from GenBank Accession No. AK108710 a 5' primer (CACCATGATGCTGCTGAGTTCCTC) (SEQ ID NO: 9) was designed and employed in a 3' RACE reaction (GeneRacer), using RNA from UV-induced indica leaves, to amplify a cDNA product of 2703 nucleotides. This was cloned into pCR4-ZeroBlunt, and completely sequenced. The derived sequence was further confirmed by cloning an identical open reading frame (2451 nucleotides) from methyl jasmonate-induced japonica seedlings by RT-PCR using the 5' primer described above and a 3' primer (TTACTCTTGCAGGTGCAGTGGCTC) (SEQ ID NO: 10). This sequence has been deposited as OsKSL11 in the various DNA databases as Accession DQ100373. Full-length and N-terminally truncated (by 60 residues) versions of OsKSL11 were constructed in pENTR/SD/D-TOPO (Gateway system) and verified by complete sequencing. These were then transferred by directional recombination to the T7-based, glutathione-S-transferase (GST) fusion expression vector pDEST15 (Gateway systems).

Recombinant expression. Recombinant expression was carried out in the BL21 derived strain C41 (Miroux and Walker 1996). Briefly, NZY media cultures were grown to midlog phase at 37° C. ($OD_{600}$~0.6) then shifted to 16° C. for 1 h prior to induction (with 1 mM IPTG) and overnight expression. Cells were harvested by centrifugation, resuspended in cold lysis buffer 50 mM Bis-Tris, pH 6.8, 1 mM DTT), lysed by mild sonication on ice (15 s, continuous output, setting 5), and clarified by centrifugation (40,000 g, 20 min). The recombinant GST-tagged protein was purified using GST-agarose beads (Sigma-Aldrich). SDS-PAGE analysis demonstrated that only a single band of the appropriate molecular weight was obtained.

Functional characterization. Assays were generally carried out with 5 μg of substrate (GGPP, syn-CPP or ent-CPP) and 25 μL of recombinant protein in 0.5 mL of assay buffer (50 mM Hepes, pH 7.2, 10 mM $MgCl_2$, 10% glycerol, and 5 mM DTT) for 3-16 h at room temperature. The assay solutions were extracted three times with 0.5 mL portions of hexanes, which were pooled, dried under a gentle stream of nitrogen, and re-dissolved in 100 μL of hexanes. Gas chromatography-mass spectrometry (GC-MS) analysis was carried out using an HP-5MS column on an Agilent (Palo Alto, Calif.) 6890N GC instrument with a 5973N mass selective detector. Samples (5 μL) were injected at 40° C. in the splitless mode and, after holding 3 min at 40° C., the temperature was increased at 20° C./min to 300° C., where it was also held for 3 min. MS data were collected from 50 to 500 m/z during the temperature ramp. Larger amounts of product were obtained from GGPP using coupled assays with purified GST-OsKSL11 and the truncated and GST-tagged version of OsCPS4 that has been previously described (Xu et al. 2004) which was expressed and purified as described above for GST-OsKSL11. The resulting hexane-benzene extract (~1 mL) containing the diterpene products was shipped to the University of Illinois on dry ice for NMR spectroscopy. The solution was filtered through a short silica gel column with pentane and then concentrated under a $N_2$ stream to ca. 0.1 mL and re-dissolved in 1 mL of $C_6D_6$. The evaporation-dissolution was repeated four times to completely remove the hexane and protonated benzene solvents. Proton NMR spectra were recorded in $C_6D_6$ (to reduce the risk of air oxidation) using a Varian 500 MHz spectrometer in the School of Chemical Sciences NMR spectroscopy facility at the University of Illinois.

Sequence analysis. BLAST searches were carried out on-line at either GenBank (www.ncbi.nih.gov), TIGR (www.tigr.org), or Gramene (www.gramene.org). All other sequence analysis was performed with the AlignX program in the Vector NTI software package (Invitrogen) using standard parameters. OsKS1 was designated as the reference sequence in all alignments.

Results

Cloning an unexpected class I terpene synthase. A putative class I labdane-related diterpene synthase gene, predicted from the rice genome sequence, was found in GenBank Accession No. AK108710. Surprisingly, when it was attempted to clone the corresponding cDNA, the isolated sequence did not correspond to that found in AK108710, although the two were ~92% identical at the nucleotide level. In fact, corresponding sequence could not be found in currently available rice genome or expressed sequence tag data, although the inventors were able to clone this cDNA from both spp. indica and japonica rice. The isolated cDNA does contain an open reading frame that encodes a class I diterpene synthase (i.e., had the large "insertional" element and DDXXD motif) that was highly homologous (42-89% amino acid identity) to the known OsKSL enzymes. (FIG. 2). Thus, it seems to be a novel kaurene synthase-like gene, which has been designated OsKSL11. The originally targeted sequence contained in AK108710 corresponds to OsKSL8, which has recently been reported to encode a transcriptionally inducible syn-CPP specific stemarene synthase. Unfortunately, OsKSL8 and OsKSL11 could not be distinguished by RT-PCR analysis due to the extensive sequence similarity, despite repeated attempts with several primer combinations designed to discriminate between the two. Therefore, it was not possible to conclusively determine if transcription of OsKSL11 is likewise induced by UV-irradiation or application of the defensive signaling molecule methyl jasmonate.

Figure 3:
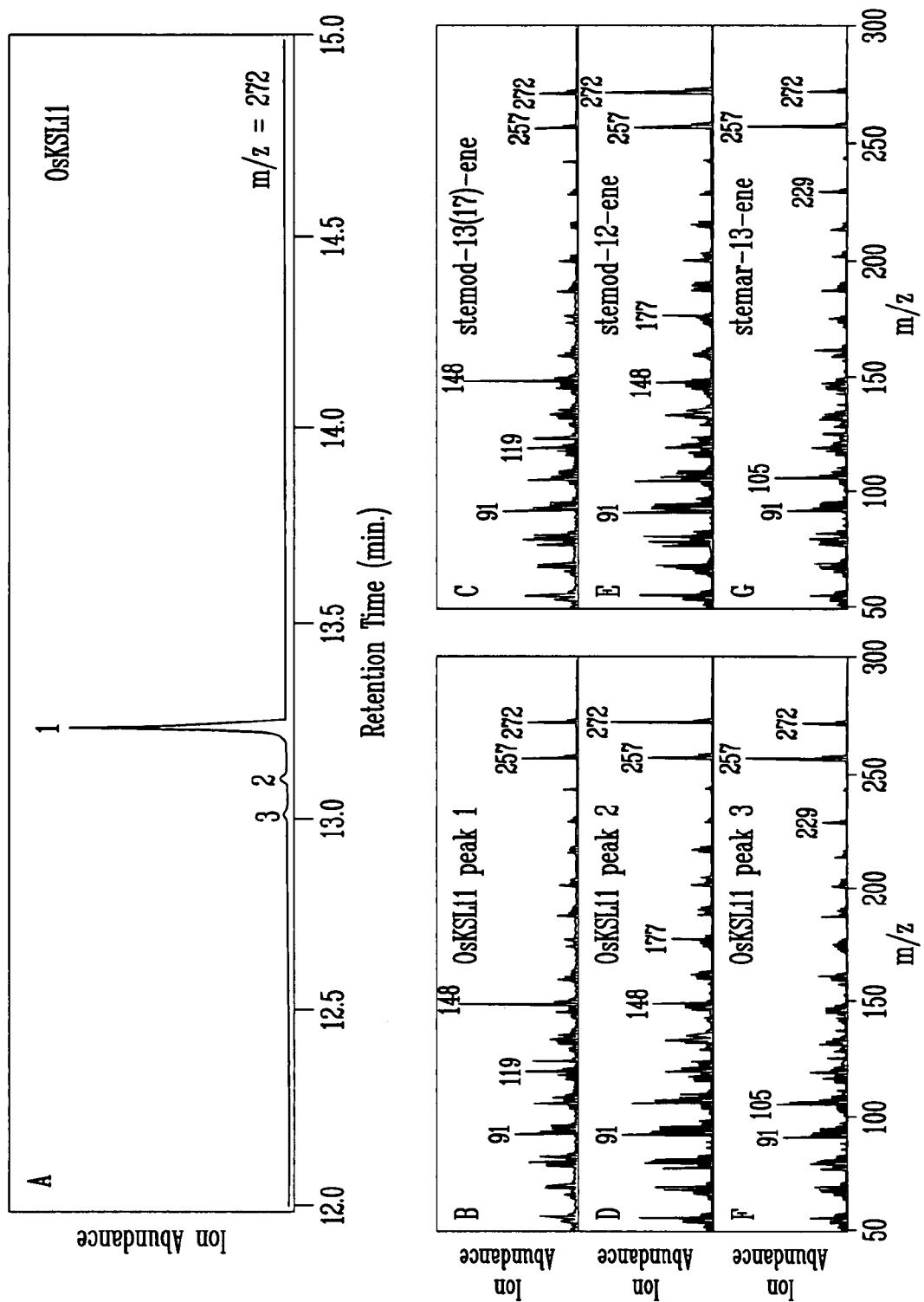
FIG. 3 illustrates the enzymatic products of OsKSL11 from syn-CPP. (A) GC-MS chromatograph (272 m/z extracted ion trace). (B) Mass spectrum of OsKSL11 product peak 1 (RT=13.23 min). (C) Mass spectrum of authentic stemod-13 (17)-ene (RT=13.23 min). (D) Mass spectrum of OsKSL11 product peak 2 (RT=13.10 min). (E) Mass spectrum of authentic stemod-12-ene (RT=13.10 min). (F) Mass spectrum of OsKSL11 product peak 3 (RT=13.01 min). (G) Mass spectrum of authentic stemar-13-ene (RT=13.01 min).

Functional characterization of OsKSL11 as a syn-CPP specific stemodene synthase. Full-length and truncated OsKSL11 proteins were expressed and purified as fusions to GST. The recombinant protein was then assayed with GGPP, ent-CPP, or syn-CPP as substrate, and enzymatic product formation assessed by GC-MS analysis of organic extracts. While the truncated construct exhibited better activity, both constructs were catalytically active only with syn-CPP, and enzymatic products were not observed with GGPP or ent-CPP. Intriguingly, GC-MS analysis demonstrated that the major enzymatic product resulting from reactions with syn-CPP did not correspond to authentic standards for any of the known rice diterpenes. (FIG. 3). To produce sufficient quantities of enzymatic product for NMR analysis, it was chosen to use a coupled assay with purified GST-tagged and truncated versions of OsCPS4 (i.e., syn-CPP synthase) and OsKSL11 (i.e. because GGPP is much more readily available than syn-CPP). In this way, it was possible to produce ~150 μg of the unknown diterpene product. Comparison of the GC-MS fragmentation pattern and NMR proton data with literature values initially suggested that OsKSL11 was producing aphidicol-16-ene. However, given the close phylogenetic relationship with syn-stemarene synthase (OsKSL8) and the fact that OsKSL11 also produces small amounts (~3%) of stemar-13-ene (endo double bond), it is strongly suspected that this product was actually the mechanistically related stemod-13(17)-ene). Synthetic (±)-stemodene, as a mixture of the exo (13(17)-ene) and endo (12-ene) double bond isomers, was obtained as a kind gift from Dr. James White. The enzymatic products of OsKSL11 with syn-CPP were then shown to be ~92% exo-stemodene, ~5% endo-stemodene, and the aforementioned ~3% endo-stemarene, by GC analyses, including GC-MS comparison to authentic samples (FIG. 3). The identification of the major product as exo-stemodene was confirmed by high field proton NMR spectra of the enzymatic product mixture and comparisons with spectra and data of the (±)-exo-stemodene standard, for which proton and carbon NMR assignments (Table 1) were made with the aid of COSY, NOE, HMQC, and APT spectral analyses.

TABLE 1

500 MHz $^1$H and 126 MHz $^{13}$C NMR data and assignments for synthetic (±)-stemod-13(17)-ene in $C_6D_6$

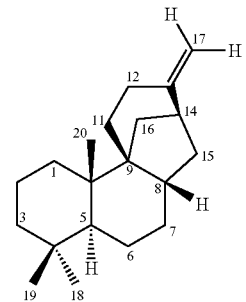

| C# | $\delta_C$ | $\delta_H$ | m | J (Hz) |
|---|---|---|---|---|
| 1 | 42.5 | Hα 1.14 | td | 12.3, 3.2 |
|   |      | Hβ 1.30-1.46 | m |  |
| 2 | 37.2 | Hα 1.52 | br d | 12.7 |
|   |      | Hβ 1.43 | qt | 12.5, 3.0 |
| 3 | 36.7 | Hα 1.07 | td | 12.8, 3.3 |
|   |      | Hβ 1.33 | dt | 13.1, 3.6 |
| 4 | 33.7 |  |  |  |
| 5 | 47.8 | 1.17 | d | 12.7 |
| 6 | 19.5 | Hα 1.30-1.46 | m |  |
|   |      | Hβ 1.11 | qd | 12.8, 3.3 |
| 7 | 23.0 | Hα 1.40 | ddd | 12.2, 7.4, 2.5 |
|   |      | Hβ 1.74-1.81 | m |  |
| 8 | 39.6 | 1.63-1.69 | m |  |
| 9 | 51.7 |  |  |  |
| 10 | 39.1 |  |  |  |
| 11 | 32.7 | Hα 1.42 | dd | 10.1, 5.2 |
|    |      | Hβ 1.40-1.42 | m |  |
| 12 | 28.9 | Hα 2.10 | ddd | 15.0, 4.4, 3.3 |
|    |      | Hβ 2.23-2.31 | m |  |
| 13 | 155.5 |  |  |  |
| 14 | 44.3 | 2.73 | t | 6.7 |
| 15 | 40.4 | Hα 1.27 | ddd | 13.8, 6.1, 2.6 |
|    |      | Hβ 1.82 | dd | 13.5, 8.1 |
| 16 | 38.2 | Hα 1.97 | ddd | 11.2, 5.6, 1.7 |
|    |      | Hβ 1.24 | d | 11.3 |
| 17 | 102.8 | HE 4.58 | t | 2.2 |
|    |       | HZ 4.67 | t | 2.4 |
| 18 | 19.2 | 0.90 | s |  |
| 19 | 23.3 | 0.89 | s |  |
| 20 | 35.1 | 0.91 | s |  |

δ: chemical shift in ppm ($C_6H_6$ reference 7.16 ppm);
m: apparent multiplicity;
J: apparent coupling constant For the above-stated reasons, it is submitted that the present invention accomplishes at least all of its stated objectives.

Having described the invention with reference to particular compositions and methods, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended.

All articles cited herein and in the following list are hereby expressly incorporated in their entirety by reference.

CITATIONS

1. S. A. Goff, et al., Science 296 (2002) 92-100.
2. J. Yu, et al., H. Yang, Science 296 (2002) 79-92.
3. R. Croteau, et al. (Eds.), Biochemistry & Molecular Biology of Plants, Am. Soc. Plant Biologists, Rockville, Md., USA, 2000, pp. 1250-1318.
4. J. Buckingham, Dictionary of Natural Products (on-line web edition), Chapman & Hall/CRC Press, 2002.
5. D. W. Cartwright, et al., Phytochemistry 20 (1981) 535-537.
6. T. Akatsuka, et al., Agric. Biol. Chem. 49 (1985) 1689-1694.
7. H. Sekido, et al., J. Pesticide Sci. 11 (1986) 369-372.
8. O. Kodama, et al., Biosci. Biotechnol. Biochem. 56 (1992) 1002-1003.
9. H. Kato, et al., Phytochemistry 33 (1993) 79-81.
10. H. Kato, et al., Phytochemistry 36 (1994) 299-301.
11. J. Koga, et al., Tetrahedron 51 (1995) 7907-7918.
12. J. Koga, et al., Phytochemistry 44 (1997) 249-253.
13. H. D. VanEtten, et al., Plant Cell 6 (1994) 1191-1192.
14. T. Kato, et al., Tetrahedron Lett. 14 (1973) 3861-3864.
15. H. Kato-Noguchi, T. Ino, Phytochemistry 63 (2003) 551-554.
16. H. Kato-Noguchi, et al., Physiologia Plantarum 115 (2002) 401-405.
17. H. P. Bais, et al., Trends Plant Sci. 9 (2004) 26-32.
18. R. S. Mohan, et al., Arch. Biochem. Biophys. 330 (1996) 33-47.
19. A. Yajima, et al., Tetrahedron Lett. 45 (2004) 167-169.
20. J. MacMillan, M. H. Beale, in: D. E. Cane (Ed.), Isoprenoids Including Carotenoids and Steroids, Elsevier Science Ltd., Oxford, 1999, pp. 217-243.
21. C. M. Starks, et al., J.P. Noel, Science 277 (1997) 1815-1820.
22. D. A. Whittington, et al., Proc Natl Acad Sci USA. 99 (2002) 15375-15380.
23. P. R. Wilderman, et al., Plant Physiol. 135 (2004) 2098-2105.
24. R. J. Peters, et al., J. Am. Chem. Soc. 123 (2001) 8974-8978.
25. E. M. Davis, R. Croteau, Top. Curr. Chem. 209 (2000) 53-95.
26. T. Sakamoto, et al., Plant Physiol. 134 (2004) 1642-1653.
27. M. Xu, et al., Plant J. 39 (2004) 309-318.
28. K. Otomo, et al., Plant J. 39 (2004) 886-893.
29. S. Prisic, et al., Plant Physiol. 136 (2004) 4228-4236.
30. K. Otomo, et al., Biosci. Biotechnol. Biochem. 68 (2004) 2001-2006.
31. E.-M. Cho, et al., Plant J. 37 (2004) 1-8.
32. T. Nemoto, et al., FEBS Lett 571 (2004) 182-186.
33. M. Margis-Pinheiro, et al., Plant Cell Reports 23 (2005) 819-833.
34. J. D. White, T. C. Somers, J. Am. Chem. Soc. 116 (1994) 9912-9920.
35. International Rice Genome Sequencing Project, Nature 436 (2005) 793-800.
36. S. Kikuchi, et al., Science 301 (2003) 376-379.
37. H. Oikawa, et al., J. Am. Chem. Soc. 123 (2001) 5154-5155.
38. P. S. Manchand, J. F. Blount, J. Chem. Soc. Chem. Commun. 1975 (1975) 894-895.
39. P. S. Manchand, et al., J. Am. Chem. Soc. 95 (1973) 2705-2706.
40. C. D. Hufford, et al., J. Nat. Prod. 54 (1991) 1543-1552.
41. J. C. D'Auria, J. Gershenzon, Curr. Opin. Plant Biol. 8 (2005) 308-316.
42. R. D. M. Page, Comput. Appl. Biosci. 12 (1996) 357-358.

What is claimed is:

1. A method of synthesizing a stemodene comprising: reacting OsKSL11 with a syn-copalyl diphosphate to produce a stemodene.

2. The method of claim 1 whereby the OsKSL11 has a polypeptide sequence as set forth in SEQ ID NO: 5.

3. The method of claim 1 whereby the stemodene is stemod-13(17)-ene.

4. The method of claim 1 further including the step of processing the stemodene to produce one or more compounds having biological activity.

* * * * *

```
SEQUENCE LISTING

<160> NUMBER OF SEQ ID NOS: 10

<210> SEQ ID NO 1
<211> LENGTH: 812
<212> TYPE: PRT
<213> ORGANISM: Oryza sativa

<400> SEQUENCE: 1

Met Met Met Leu Leu Leu Pro Ser Ser Ser Ser Ser Cys Cys Cys Arg
1               5                   10                  15

Cys Pro Gly Gly Gln Phe His Gly Ala Pro Pro Arg Val Met Ala Pro
            20                  25                  30

Arg Arg Gly Val Thr Arg Val Tyr Ile Glu Lys Arg Leu Gly Val Gly
        35                  40                  45

Gly Gly Asn Ala Ser Ser Leu Gln Asp Met His Arg Lys Glu Leu Gln
    50                  55                  60

Ala Arg Thr Arg Asp Gln Leu Gln Thr Leu Glu Leu Ser Thr Ser Leu
65                  70                  75                  80
```

-continued

```
Tyr Asp Thr Ala Trp Val Ala Met Val Pro Leu Arg Gly Ser Arg Gln
                85                  90                  95
His Pro Cys Phe Pro Gln Cys Val Glu Trp Ile Leu Gln Asn Gln Gln
            100                 105                 110
Asp Asp Gly Ser Trp Gly Thr Arg Gly Phe Gly Val Ala Val Thr Arg
        115                 120                 125
Asp Val Leu Ser Ser Thr Leu Ala Cys Val Leu Ala Leu Lys Arg Trp
    130                 135                 140
Asn Val Gly Gln Glu His Ile Arg Arg Gly Leu Asp Phe Ile Gly Arg
145                 150                 155                 160
Asn Phe Ser Ile Ala Met Asp Glu Gln Ile Ala Ala Pro Val Gly Phe
                165                 170                 175
Asn Ile Thr Phe Pro Gly Met Leu Ser Leu Ala Met Gly Met Asp Leu
            180                 185                 190
Glu Phe Pro Val Arg Gln Thr Asp Val Asp Arg Leu Leu His Leu Arg
        195                 200                 205
Glu Ile Glu Leu Glu Arg Glu Ala Gly Asp His Ser Tyr Gly Arg Lys
    210                 215                 220
Ala Tyr Met Ala Tyr Val Thr Glu Gly Leu Gly Asn Leu Leu Glu Trp
225                 230                 235                 240
Asp Glu Ile Met Met Phe Gln Arg Lys Asn Gly Ser Phe Phe Asn Cys
                245                 250                 255
Pro Ser Thr Thr Ala Ala Thr Leu Val Asn His Tyr Asn Asp Lys Ala
            260                 265                 270
Leu Gln Tyr Leu Asn Cys Leu Val Ser Lys Phe Gly Ser Ala Val Pro
        275                 280                 285
Thr Val Tyr Pro Leu Asn Ile Tyr Cys Gln Leu Ser Trp Val Asp Ala
    290                 295                 300
Leu Glu Lys Met Gly Ile Ser Gln Tyr Phe Val Ser Glu Ile Lys Ser
305                 310                 315                 320
Ile Leu Asp Thr Thr Tyr Val Ser Trp Leu Glu Arg Asp Glu Glu Ile
                325                 330                 335
Met Leu Asp Ile Thr Thr Cys Ala Met Ala Phe Arg Leu Leu Arg Met
            340                 345                 350
Asn Gly Tyr His Val Ser Ser Val Glu Leu Ser Pro Val Ala Glu Ala
        355                 360                 365
Ser Ser Phe Arg Glu Ser Leu Gln Gly Tyr Leu Asn Asp Lys Lys Ser
    370                 375                 380
Leu Ile Glu Leu Tyr Lys Ala Ser Lys Val Ser Lys Ser Glu Asn Glu
385                 390                 395                 400
Ser Ile Leu Asp Ser Ile Gly Ser Trp Ser Gly Ser Leu Leu Lys Glu
                405                 410                 415
Ser Val Cys Ser Asn Gly Val Lys Lys Ala Pro Ile Phe Glu Glu Met
            420                 425                 430
Lys Tyr Ala Leu Lys Phe Pro Phe Tyr Thr Thr Leu Asp Arg Leu Asp
        435                 440                 445
His Lys Arg Asn Ile Glu Arg Phe Asp Ala Lys Asp Ser Gln Met Leu
    450                 455                 460
Lys Thr Glu Tyr Leu Leu Pro His Ala Asn Gln Asp Ile Leu Ala Leu
465                 470                 475                 480
Ala Val Glu Asp Phe Ser Ser Ser Gln Ser Ile Tyr Gln Asp Glu Leu
                485                 490                 495
```

```
Asn Tyr Leu Glu Cys Trp Val Lys Asp Glu Lys Leu Asp Gln Leu Pro
            500                 505                 510

Phe Ala Arg Gln Lys Leu Thr Tyr Cys Tyr Leu Ser Ala Ala Ala Thr
            515                 520                 525

Ile Phe Pro Arg Glu Leu Ser Glu Ala Arg Ile Ala Trp Ala Lys Asn
            530                 535                 540

Gly Val Leu Thr Thr Val Val Asp Asp Phe Phe Asp Leu Gly Gly Ser
545                 550                 555                 560

Lys Glu Glu Leu Glu Asn Leu Ile Ala Leu Val Glu Lys Trp Asp Gly
            565                 570                 575

His Gln Glu Glu Phe Tyr Ser Glu Gln Val Arg Ile Val Phe Ser Ala
            580                 585                 590

Ile Tyr Thr Thr Val Asn Gln Leu Gly Ala Lys Ala Ser Ala Leu Gln
            595                 600                 605

Gly Arg Asp Val Thr Lys His Leu Thr Glu Ile Trp Leu Cys Leu Met
            610                 615                 620

Arg Ser Met Met Thr Glu Ala Glu Trp Gln Arg Thr Lys Tyr Val Pro
625                 630                 635                 640

Thr Met Glu Glu Tyr Met Ala Asn Ala Val Val Ser Phe Ala Leu Gly
            645                 650                 655

Pro Ile Val Leu Pro Thr Leu Tyr Phe Val Gly Pro Lys Leu Gln Glu
            660                 665                 670

Asp Val Val Arg Asp His Glu Tyr Asn Glu Leu Phe Arg Leu Met Ser
            675                 680                 685

Thr Cys Gly Arg Leu Leu Asn Asp Ser Gln Gly Phe Glu Arg Glu Ser
            690                 695                 700

Leu Glu Gly Lys Leu Asn Ser Val Ser Leu Leu Val His His Ser Gly
705                 710                 715                 720

Gly Ser Ile Ser Ile Asp Glu Ala Lys Met Lys Ala Gln Lys Ser Ile
            725                 730                 735

Asp Thr Ser Arg Arg Asn Leu Leu Arg Leu Val Leu Gly Glu Gln Gly
            740                 745                 750

Ala Val Pro Arg Pro Cys Lys Gln Leu Phe Trp Lys Met Cys Lys Ile
            755                 760                 765

Val His Met Phe Tyr Ser Arg Thr Asp Gly Phe Ser Ser Pro Lys Glu
            770                 775                 780

Met Val Ser Ala Val Asn Ala Val Val Lys Glu Pro Leu Lys Leu Lys
785                 790                 795                 800

Val Ser Asp Pro Tyr Gly Ser Ile Leu Ser Gly Asn
            805                 810

<210> SEQ ID NO 2
<211> LENGTH: 837
<212> TYPE: PRT
<213> ORGANISM: Oryza sativa

<400> SEQUENCE: 2

Met Met Leu Leu Gly Ser Pro Ser Ser Gly Tyr Gly Gly Lys Phe
1               5                   10                  15

Ala Gly Ala Ser Pro Ala Gly Gly Thr Thr Met Ala Pro Ser Ala
            20                  25                  30

Lys Gln Pro Ser Ser Arg Ala Pro Pro Gly Ile Thr Gly Gly Arg
            35                  40                  45

Asn Asp Leu Arg Ile Leu Ser Pro Ala Ala Ala Ala Ala Val Gly
50                  55                  60
```

-continued

```
Gly Leu Glu Met Lys Lys Pro Glu Ala Glu Gly Ile Ala Glu Ser Leu
65                  70                  75                  80

Gln Ala Thr His Arg Lys Glu Leu Glu Ala Ser Ile Arg Lys Gln Leu
                85                  90                  95

Gln Thr Leu Glu Leu Ser Thr Ser Leu Tyr Asp Thr Ala Trp Val Ala
            100                 105                 110

Met Val Pro Leu Arg Gly Ser Arg Gln His Pro Cys Phe Pro Gln Cys
        115                 120                 125

Val Glu Trp Ile Leu Gln Asn Gln Gln Asp Asp Gly Ser Trp Gly Thr
    130                 135                 140

Arg Gly Phe Gly Val Ala Val Thr Arg Asp Val Leu Ser Ser Thr Leu
145                 150                 155                 160

Ala Cys Val Leu Ala Leu Lys Arg Trp Asn Val Gly Gln Glu His Ile
                165                 170                 175

Arg Arg Gly Leu Asp Phe Ile Gly Arg Asn Phe Ser Ile Ala Met Asp
            180                 185                 190

Glu Gln Ile Ala Ala Pro Val Gly Phe Asn Ile Thr Phe Pro Gly Met
        195                 200                 205

Leu Ser Leu Ala Met Gly Met Asp Leu Glu Phe Pro Val Arg Gln Thr
    210                 215                 220

Asp Val Asp Arg Leu Leu His Leu Arg Glu Ile Glu Leu Glu Arg Glu
225                 230                 235                 240

Ala Gly Asp His Ser Tyr Gly Arg Lys Ala Tyr Met Ala Tyr Val Thr
                245                 250                 255

Glu Gly Leu Gly Asn Leu Leu Glu Trp Asp Glu Ile Met Met Phe Gln
            260                 265                 270

Arg Lys Asn Gly Ser Phe Phe Asn Cys Pro Ser Thr Thr Ala Ala Thr
        275                 280                 285

Leu Val Asn His Tyr Asn Asp Lys Ala Leu Gln Tyr Leu Asn Cys Leu
    290                 295                 300

Val Ser Lys Phe Gly Ser Ala Val Pro Thr Val Tyr Pro Leu Asn Ile
305                 310                 315                 320

Tyr Cys Gln Leu Ser Trp Val Asp Ala Leu Glu Lys Met Gly Ile Ser
                325                 330                 335

Gln Tyr Phe Val Ser Glu Ile Lys Ser Ile Leu Asp Thr Thr Tyr Val
            340                 345                 350

Ser Trp Leu Glu Arg Asp Glu Glu Ile Met Leu Asp Ile Thr Thr Cys
        355                 360                 365

Ala Met Ala Phe Arg Leu Leu Arg Met Asn Gly Tyr His Val Ser Ser
    370                 375                 380

Val Glu Leu Ser Pro Val Ala Glu Ala Ser Ser Phe Arg Glu Ser Leu
385                 390                 395                 400

Gln Gly Tyr Leu Asn Asp Lys Lys Ser Leu Ile Glu Leu Tyr Lys Ala
                405                 410                 415

Ser Lys Val Ser Lys Ser Glu Asn Glu Ser Ile Leu Asp Ser Ile Gly
            420                 425                 430

Ser Trp Ser Gly Ser Leu Leu Lys Glu Ser Val Cys Ser Asn Gly Val
        435                 440                 445

Lys Lys Ala Pro Ile Phe Glu Glu Met Lys Tyr Ala Leu Lys Phe Pro
    450                 455                 460

Phe Tyr Thr Thr Leu Asp Arg Leu Asp His Lys Arg Asn Ile Glu Arg
465                 470                 475                 480
```

```
Phe Asp Ala Lys Asp Ser Gln Met Leu Lys Thr Glu Tyr Leu Leu Pro
            485                 490                 495

His Ala Asn Gln Asp Ile Leu Ala Leu Ala Val Glu Asp Phe Ser Ser
            500                 505                 510

Ser Gln Ser Ile Tyr Gln Asp Glu Leu Asn Tyr Leu Glu Cys Trp Val
            515                 520                 525

Lys Asp Glu Lys Leu Asp Gln Leu Pro Phe Ala Arg Gln Lys Leu Thr
            530                 535                 540

Tyr Cys Tyr Leu Ser Ala Ala Thr Ile Phe Pro Arg Glu Leu Ser
545                 550                 555                 560

Glu Ala Arg Ile Ala Trp Ala Lys Asn Gly Val Leu Thr Val Val
                565                 570                 575

Asp Asp Phe Phe Asp Leu Gly Gly Ser Lys Glu Glu Leu Glu Asn Leu
            580                 585                 590

Ile Ala Leu Val Glu Lys Trp Asp Gly His Gln Glu Glu Phe Tyr Ser
            595                 600                 605

Glu Gln Val Arg Ile Val Phe Ser Ala Ile Tyr Thr Thr Val Asn Gln
            610                 615                 620

Leu Gly Ala Lys Ala Ser Ala Leu Gln Gly Arg Asp Val Thr Lys His
625                 630                 635                 640

Leu Thr Glu Ile Trp Leu Cys Leu Met Arg Ser Met Met Thr Glu Ala
                645                 650                 655

Glu Trp Gln Arg Thr Lys Tyr Val Pro Thr Met Glu Glu Tyr Met Ala
            660                 665                 670

Asn Ala Val Val Ser Phe Ala Leu Gly Pro Ile Val Leu Pro Thr Leu
            675                 680                 685

Tyr Phe Val Gly Pro Lys Leu Gln Glu Asp Val Val Arg Asp His Glu
            690                 695                 700

Tyr Asn Glu Leu Phe Arg Leu Met Ser Thr Cys Gly Arg Leu Leu Asn
705                 710                 715                 720

Asp Ser Gln Gly Phe Glu Arg Glu Ser Leu Glu Gly Lys Leu Asn Ser
            725                 730                 735

Val Ser Leu Leu Val His His Ser Gly Gly Ser Ile Ser Ile Asp Glu
            740                 745                 750

Ala Lys Met Lys Ala Gln Lys Ser Ile Asp Thr Ser Arg Arg Asn Leu
            755                 760                 765

Leu Arg Leu Val Leu Gly Glu Gln Gly Ala Val Pro Arg Pro Cys Lys
            770                 775                 780

Gln Leu Phe Trp Lys Met Cys Lys Ile Val His Met Phe Tyr Ser Arg
785                 790                 795                 800

Thr Asp Gly Phe Ser Ser Pro Lys Glu Met Val Ser Ala Val Asn Ala
            805                 810                 815

Val Val Lys Glu Pro Leu Lys Leu Lys Val Ser Asp Pro Tyr Gly Ser
            820                 825                 830

Ile Leu Ser Gly Asn
        835

<210> SEQ ID NO 3
<211> LENGTH: 836
<212> TYPE: PRT
<213> ORGANISM: Oryza sativa

<400> SEQUENCE: 3

Met Glu Ala Val Ala Arg Ser Ser Leu Val Leu Ala Pro Arg Arg Arg
1               5                   10                  15
```

-continued

```
Arg Ala Leu Gly Leu Leu Pro Ala Ala Ala Pro Phe Val Leu Asp
             20                  25                  30

Cys Arg Arg Arg His Asn Gly Met Arg Arg Pro His Val Ser Phe
         35                  40                  45

Ala Cys Ser Ala Glu Leu Asp Thr Gly Arg Arg Gln Leu Pro Ser Thr
 50                  55                  60

Gly Thr Arg Ala Val Met Ser Ser Cys Pro Gly Tyr Val Glu Gly Arg
 65                  70                  75                  80

Met Val Gly Glu Asn Thr Ser Gln Ile Asn Met Gly Arg Glu Ala Arg
                 85                  90                  95

Ile Arg Arg His Leu Glu Asn Pro Glu Phe Leu Pro Ser Ser Tyr Asp
             100                 105                 110

Ile Ala Trp Val Ala Met Val Pro Leu Pro Gly Thr Asp His Leu Gln
         115                 120                 125

Ala Pro Cys Phe Pro Glu Cys Val Glu Trp Ile Leu Gln Asn Gln His
130                 135                 140

Ser Asn Gly Ser Trp Gly Val Asn Glu Phe Asp Ser Ser Ala Ser Lys
145                 150                 155                 160

Asp Ile Leu Leu Ser Thr Leu Ala Cys Ile Ile Ala Leu Glu Lys Trp
                165                 170                 175

Asn Val Gly Ser Glu Gln Ile Arg Arg Gly Leu His Phe Ile Ala Lys
            180                 185                 190

Asn Phe Ser Ile Val Ile Asp Asp Gln Ile Ala Ala Pro Ile Gly Phe
        195                 200                 205

Asn Leu Thr Phe Pro Ala Met Val Asn Leu Ala Ile Lys Met Gly Leu
    210                 215                 220

Glu Phe Pro Ala Ser Glu Ile Ser Ile Asp Gln Ile Leu His Leu Arg
225                 230                 235                 240

Asp Met Glu Leu Lys Arg Leu Ser Gly Glu Glu Ser Leu Gly Lys Glu
                245                 250                 255

Ala Tyr Phe Ala Tyr Ile Ala Glu Gly Leu Glu Glu Ser Met Val Asp
            260                 265                 270

Trp Ser Glu Val Met Lys Phe Gln Gly Lys Asn Gly Ser Leu Phe Asn
        275                 280                 285

Ser Pro Ala Ala Thr Ala Ala Leu Val His Arg Tyr Asp Asp Lys
    290                 295                 300

Ala Leu Gly Tyr Leu Tyr Ser Val Val Asn Lys Phe Gly Gly Glu Val
305                 310                 315                 320

Pro Thr Val Tyr Pro Leu Asn Ile Phe Ser Gln Leu Ser Met Val Asp
                325                 330                 335

Thr Leu Val Asn Ile Gly Ile Ser Arg His Phe Ser Ser Asp Ile Lys
            340                 345                 350

Arg Ile Leu Asp Lys Thr Tyr Ile Leu Trp Ser Gln Arg Asp Glu Glu
        355                 360                 365

Val Met Leu Asp Leu Pro Thr Cys Ala Met Ala Phe Arg Leu Leu Arg
    370                 375                 380

Met Asn Gly Tyr Gly Val Ser Ser Asp Asp Leu Ser His Val Ala Glu
385                 390                 395                 400

Ala Ser Thr Phe His Asn Ser Val Glu Gly Tyr Leu Asp Asp Thr Lys
                405                 410                 415

Ser Leu Leu Glu Leu Tyr Lys Ala Ser Lys Val Ser Leu Ser Glu Asn
            420                 425                 430
```

```
Glu Pro Ile Leu Glu Lys Met Gly Cys Trp Ser Gly Ser Leu Leu Lys
            435                 440                 445

Glu Lys Leu Cys Ser Asp Asp Ile Arg Gly Thr Pro Ile Leu Gly Glu
        450                 455                 460

Val Glu Tyr Ala Leu Lys Phe Pro Phe Tyr Ala Thr Leu Glu Pro Leu
465                 470                 475                 480

Asp His Lys Trp Asn Ile Glu Asn Phe Asp Ala Arg Ala Tyr Gln Lys
                485                 490                 495

Ile Lys Thr Lys Asn Met Pro Cys His Val Asn Glu Asp Leu Leu Ala
            500                 505                 510

Leu Ala Ala Glu Asp Phe Ser Phe Cys Gln Ser Thr Tyr Gln Asn Glu
        515                 520                 525

Ile Gln His Leu Glu Ser Trp Glu Lys Glu Asn Lys Leu Asp Gln Leu
        530                 535                 540

Glu Phe Thr Arg Lys Asn Leu Ile Asn Ser Tyr Leu Ser Ala Ala Ala
545                 550                 555                 560

Thr Ile Ser Pro Tyr Glu Leu Ser Asp Ala Arg Ile Ala Cys Ala Lys
                565                 570                 575

Ser Ile Ala Leu Thr Leu Val Ala Asp Asp Phe Phe Asp Val Gly Ser
            580                 585                 590

Ser Lys Glu Glu Gln Glu Asn Leu Ile Ser Leu Val Glu Lys Trp Asp
        595                 600                 605

Gln Tyr His Lys Val Glu Phe Tyr Ser Glu Asn Val Lys Ala Val Phe
        610                 615                 620

Phe Ala Leu Tyr Ser Thr Val Asn Gln Leu Gly Ala Met Ala Ser Ala
625                 630                 635                 640

Val Gln Asn Arg Asp Val Thr Lys Tyr Asn Val Glu Ser Trp Leu Asp
                645                 650                 655

Tyr Leu Arg Ser Leu Ala Thr Asp Ala Glu Trp Gln Arg Ser Lys Tyr
            660                 665                 670

Val Pro Thr Met Glu Glu Tyr Met Lys Asn Ser Ile Val Thr Phe Ala
        675                 680                 685

Leu Gly Pro Thr Ile Leu Ile Ala Leu Tyr Phe Met Gly Gln Asn Leu
        690                 695                 700

Trp Glu Asp Ile Val Lys Asn Ala Glu Tyr Asp Glu Leu Phe Arg Leu
705                 710                 715                 720

Met Asn Thr Cys Gly Arg Leu Gln Asn Asp Ile Gln Ser Phe Glu Arg
                725                 730                 735

Glu Cys Lys Asp Gly Lys Leu Asn Ser Val Ser Leu Leu Val Leu Asp
            740                 745                 750

Ser Lys Asp Val Met Ser Val Glu Glu Ala Lys Glu Ala Ile Asn Glu
        755                 760                 765

Ser Ile Ser Ser Cys Arg Arg Glu Leu Leu Arg Leu Val Val Arg Glu
        770                 775                 780

Asp Gly Val Ile Pro Lys Ser Cys Lys Glu Met Phe Trp Asn Leu Tyr
785                 790                 795                 800

Lys Thr Ser His Val Phe Tyr Ser Gln Ala Asp Gly Phe Ser Ser Pro
                805                 810                 815

Lys Glu Met Met Gly Ala Met Asn Gly Val Ile Phe Glu Pro Leu Lys
            820                 825                 830

Thr Arg Gly Asn
        835
```

<210> SEQ ID NO 4
<211> LENGTH: 806
<212> TYPE: PRT
<213> ORGANISM: Oryza sativa

<400> SEQUENCE: 4

```
Met Leu Pro Ser Ser Ile Cys Ser Met Gly Gln Ile Pro Arg Thr Ser
 1               5                  10                  15
Pro His Tyr Tyr Gly Met Leu Pro Lys Gln Met Ser Lys Gly His Pro
             20                  25                  30
Pro Met Val Thr Arg Ala Val Gly Gly Val Glu Lys Gly Glu Val Gly
         35                  40                  45
Gly Asn Val Arg Ser Leu Gln Val Met His Ser Lys Glu Leu Gln Ala
     50                  55                  60
Lys Ile Arg Arg Gln Leu Gln Arg Val Glu Leu Ser Pro Ser Leu Tyr
 65                  70                  75                  80
Asp Thr Ala Trp Val Ala Met Val Pro Glu Arg Ser Ser Ser Gln Ala
                 85                  90                  95
Pro Cys Tyr Pro Gln Cys Ile Glu Trp Ile Leu Gln Asn Gln His Asp
            100                 105                 110
Asp Gly Ser Trp Gly Ile Asn Ser Ser Ser Leu Ser Val Asn Lys Asp
        115                 120                 125
Ile Leu Leu Ser Thr Leu Ala Cys Val Val Ala Leu Lys Lys Trp Asn
    130                 135                 140
Ala Gly Ser Tyr His Ile Lys Arg Gly Leu Asn Phe Val Gly Arg Asn
145                 150                 155                 160
Phe Ser Val Ala Met Asp Val Gln Asn Ile Ala Pro Val Gly Phe Asn
                165                 170                 175
Val Thr Phe Ser Gly Leu Ile Thr Leu Ala Ser Gly Met Gly Leu Gln
            180                 185                 190
Leu Pro Val Trp Gln Thr Asp Ile Asp Glu Ile Phe His Leu Arg Lys
        195                 200                 205
Ile Glu Leu Glu Arg Asp Ser Gly Gly Thr Ile Ser Ala Arg Lys Ala
    210                 215                 220
Phe Met Ala Tyr Val Ala Glu Gly Phe Gly Ser Leu Gln Asp Trp Asp
225                 230                 235                 240
Gln Val Met Ala Tyr Gln Arg Lys Asn Gly Ser Leu Phe Asn Ser Pro
                245                 250                 255
Ser Thr Thr Ala Ala Ala Ile His Thr Phe Asn Asp Arg Thr Leu
            260                 265                 270
Asn Tyr Leu Asp Ser Leu Thr Asn Lys Phe Gly Gly Pro Val Pro Ala
        275                 280                 285
Met Tyr Pro Gln Asn Ile Tyr Ser Gln Leu Cys Thr Val Asp Ala Leu
    290                 295                 300
Glu Arg Thr Gly Ile Ser Gln Lys Phe Ala Arg Glu Ile Arg Asp Ile
305                 310                 315                 320
Leu Asp Thr Thr Tyr Arg Ser Trp Leu His Asn Glu Glu Val Met
                325                 330                 335
Leu Asp Ile Pro Thr Cys Ala Met Ala Phe Arg Leu Leu Arg Thr His
            340                 345                 350
Gly Tyr Asp Ile Thr Ser Asp Glu Met Ala His Phe Ser Glu Gln Ser
        355                 360                 365
Ser Phe Asp Asp Ser Ile His Gly Tyr Leu Asn Asp Thr Lys Thr Leu
    370                 375                 380
```

```
Leu Glu Leu Phe Lys Thr Ser Gln Ile Arg Phe Ser Cys Glu Asp Leu
385                 390                 395                 400

Val Leu Glu Asn Ile Gly Thr Trp Ser Ala Lys Leu Leu Lys Gln Gln
            405                 410                 415

Leu Leu Ser Asn Lys Leu Ser Thr Ser Ala Gln Ser Glu Val Glu Tyr
            420                 425                 430

Val Leu Lys Phe Pro Leu His Ser Thr Leu Asp Arg Leu Glu His Arg
            435                 440                 445

Arg Asn Ile Glu Gln Phe Lys Val Glu Gly Ser Lys Val Leu Lys Ser
    450                 455                 460

Gly Tyr Cys Gly Ser His Ser Asn Glu Glu Ile Leu Ala Leu Ala Val
465                 470                 475                 480

Asp Tyr Phe His Ser Ser Gln Ser Val Tyr Gln Gln Glu Leu Lys Tyr
                485                 490                 495

Phe Glu Ser Trp Val Lys Gln Cys Arg Leu Asp Glu Leu Lys Phe Ala
                500                 505                 510

Arg Val Met Pro Leu Ile Val His Phe Ser Ala Ala Thr Ile Phe
            515                 520                 525

Ala Pro Glu Leu Ala Asp Ala Arg Met Val Leu Ser Gln Thr Cys Met
530                 535                 540

Leu Ile Thr Val Tyr Asp Asp Phe Phe Asp Cys Pro Glu Ile Ser Arg
545                 550                 555                 560

Glu Glu Lys Glu Asn Tyr Ile Ala Leu Ile Glu Lys Trp Asp Asn His
            565                 570                 575

Ala Glu Ile Gly Phe Cys Ser Lys Asn Val Glu Ile Val Phe Tyr Ala
            580                 585                 590

Val Tyr Asn Thr Tyr Lys Gln Ile Gly Glu Lys Ala Ala Leu Lys Gln
            595                 600                 605

Asn Arg Ser Ile Met Asp Gln Leu Val Glu Asp Leu Val Ser Ser Ala
    610                 615                 620

Lys Ala Met Met Val Glu Ala Asp Trp Thr Ala Thr Lys Tyr Ile Pro
625                 630                 635                 640

Ala Thr Met Glu Glu Tyr Met Ser Asn Ala Glu Val Ser Gly Ala Phe
                645                 650                 655

Ala Ser Phe Val Cys Pro Pro Leu Tyr Phe Leu Gly Leu Lys Leu Ser
                660                 665                 670

Glu Glu Asp Val Lys Ser His Glu Tyr Thr Gln Leu Leu Lys Leu Thr
            675                 680                 685

Asn Val Ile Gly Arg Leu Gln Asn Asp Ser Gln Thr Tyr Arg Lys Glu
            690                 695                 700

Ile Leu Ala Gly Lys Val Asn Ser Val Leu Arg Ala Leu Thr Asp
705                 710                 715                 720

Ser Gly Asn Thr Ser Pro Glu Ser Ile Glu Ala Ala Lys Glu Ile Val
            725                 730                 735

Asn Arg Asp Ala Glu Ser Ser Met Val Glu Gly Pro Ile Pro Arg Pro
            740                 745                 750

Cys Lys Asp Arg Phe Trp Glu Met Cys Lys Ile Val Phe Tyr Phe Tyr
            755                 760                 765

Ser Glu Asp Asp Ala Tyr Arg Thr Pro Lys Glu Thr Met Ser Ser Ala
            770                 775                 780

Arg Ala Val Ile Leu Asp Pro Leu Arg Leu Ile Pro Pro Pro Ser Cys
785                 790                 795                 800

Pro Glu Thr Leu Ser Ser
```

<210> SEQ ID NO 5
<211> LENGTH: 816
<212> TYPE: PRT
<213> ORGANISM: Oryza sativa

<400> SEQUENCE: 5

Met Met Leu Leu Ser Ser Ser Tyr Ser Gly Gly Gln Phe Pro Gly Val
1               5                   10                  15

Ser Pro Leu Gly Thr Arg Pro Lys Arg Ser Thr Thr Val Val Pro Leu
            20                  25                  30

Pro Val Val Thr Arg Ala Thr Ala Gly Gly Val Arg Asn Asn Leu Glu
        35                  40                  45

Val Val Gly Asn Ala Gly Thr Leu Gln Gly Met Asp Ile Asp Glu Leu
    50                  55                  60

Arg Val Ile Val Arg Lys Gln Leu Gln Gly Val Glu Leu Ser Pro Ser
65                  70                  75                  80

Ser Tyr Asp Thr Ala Trp Val Ala Met Val Pro Val Gln Gly Ser Pro
                85                  90                  95

Gln Ser Pro Cys Phe Pro Gln Cys Val Glu Trp Ile Leu Gln Asn Gln
            100                 105                 110

Gln Glu Asp Gly Ser Trp Gly His Ser Ala Gly Pro Ser Gly Glu Val
        115                 120                 125

Asn Lys Asp Ile Leu Leu Ser Thr Leu Ala Cys Val Leu Ala Leu Asn
    130                 135                 140

Thr Trp Asn Val Gly Gln Asp His Ile Arg Arg Gly Leu Ser Phe Ile
145                 150                 155                 160

Gly Arg Asn Phe Ser Val Ala Ile Asp Gly Gln Cys Ala Ala Pro Val
                165                 170                 175

Gly Phe Asn Ile Thr Phe Ser Gly Met Leu His Leu Ala Ile Gly Met
            180                 185                 190

Gly Leu Lys Phe Pro Val Met Glu Thr Asp Ile Asp Ser Ile Phe Arg
        195                 200                 205

Leu Arg Glu Val Glu Phe Glu Arg Asp Ala Gly Gly Thr Ala Ser Ala
    210                 215                 220

Arg Lys Ala Phe Met Ala Tyr Val Ser Glu Gly Leu Gly Arg Glu Gln
225                 230                 235                 240

Asp Trp Asp His Val Met Ala Tyr Gln Arg Lys Asn Gly Ser Leu Phe
                245                 250                 255

Asn Ser Pro Ser Thr Thr Ala Ala Ser Ala Ile His Ser Cys Asn Asp
            260                 265                 270

Arg Ala Leu Asp Tyr Leu Val Ser Leu Thr Ser Lys Leu Gly Gly Pro
        275                 280                 285

Val Pro Ala Ile His Pro Asp Lys Val Tyr Ser Gln Leu Cys Met Val
    290                 295                 300

Asp Thr Leu Glu Lys Met Gly Ile Ser Ser Asp Phe Ala Cys Asp Ile
305                 310                 315                 320

Arg Asp Ile Leu Asp Met Thr Tyr Ser Cys Trp Met Gln Asp Glu Glu
                325                 330                 335

Glu Ile Met Leu Asp Met Ala Thr Cys Ala Lys Ala Phe Arg Leu Leu
            340                 345                 350

Arg Met His Gly Tyr Asp Val Ser Ser Glu Gly Met Ala Arg Phe Ala
        355                 360                 365

-continued

Glu Arg Ser Ser Phe Asp Asp Ser Ile His Ala Tyr Leu Asn Asp Thr
370                 375                 380

Lys Pro Leu Leu Glu Leu Tyr Lys Ser Ser Gln Leu His Phe Leu Glu
385                 390                 395                 400

Glu Asp Leu Ile Leu Glu Asn Ile Ser Ser Trp Ser Ala Lys Leu Leu
                405                 410                 415

Lys Gln Gln Leu Ser Ser Asn Lys Ile Met Lys Ser Leu Met Pro Glu
            420                 425                 430

Val Glu Tyr Ala Leu Lys Tyr Pro Leu Tyr Ser Thr Val Asp Ala Leu
        435                 440                 445

Glu His Arg Gly Asn Ile Glu Arg Phe Asn Val Asn Gly Phe Gln Arg
    450                 455                 460

Pro Lys Ser Gly Tyr Cys Gly Ser Gly Ala Asp Lys Glu Ile Leu Ala
465                 470                 475                 480

Leu Ala Val Asp Lys Phe His Tyr Asn Gln Ser Val Tyr Gln Gln Glu
                485                 490                 495

Leu Arg Tyr Leu Glu Ser Trp Val Ala Glu Phe Gly Leu Asp Glu Leu
            500                 505                 510

Lys Phe Ala Arg Val Ile Pro Leu Gln Ser Leu Leu Ser Ala Leu Val
        515                 520                 525

Pro Leu Phe Pro Ala Glu Leu Ser Asp Ala Arg Ile Ala Phe Ser Gln
    530                 535                 540

Asn Cys Met Leu Thr Thr Met Val Asp Phe Phe Asp Gly Gly Gly
545                 550                 555                 560

Ser Met Glu Glu Met Val Asn Phe Val Ala Leu Ile Asp Glu Trp Asp
                565                 570                 575

Asn His Gly Glu Ile Gly Phe Cys Ser Asn Asn Val Glu Ile Met Phe
            580                 585                 590

Asn Ala Ile Tyr Asn Thr Thr Lys Arg Asn Cys Ala Lys Ala Ala Leu
        595                 600                 605

Val Gln Asn Arg Cys Val Met Asp His Ile Ala Lys Gln Trp Gln Val
    610                 615                 620

Met Val Arg Ala Met Lys Thr Glu Ala Glu Trp Ala Ala Ser Arg His
625                 630                 635                 640

Ile Pro Ala Thr Met Glu Glu Tyr Met Ser Val Gly Glu Pro Ser Phe
                645                 650                 655

Ala Leu Gly Pro Ile Val Pro Leu Ser Ala Tyr Leu Leu Gly Glu Glu
            660                 665                 670

Leu Pro Glu Glu Ala Val Arg Ser Pro Glu Tyr Gly Gln Leu Leu Arg
        675                 680                 685

His Ala Ser Ala Val Gly Arg Leu Leu Asn Asp Val Met Thr Tyr Glu
    690                 695                 700

Lys Glu Val Leu Thr Trp Thr Pro Asn Ser Val Leu Leu Gln Ala Leu
705                 710                 715                 720

Ala Ala Ala Arg Gly Gly Gly Glu Ser Pro Thr Pro Ser Pro Ala
                725                 730                 735

Cys Ala Glu Ala Ala Arg Gly Glu Val Arg Arg Ala Ile Gln Ala Ser
            740                 745                 750

Trp Arg Asp Leu His Arg Leu Val Phe Arg Asp Asp Gly Ser Ser
        755                 760                 765

Ile Val Pro Arg Ala Cys Arg Glu Leu Phe Trp Gly Thr Ala Lys Val
    770                 775                 780

Ala Asn Val Phe Tyr Gln Glu Val Asp Gly Tyr Thr Pro Lys Ala Met

```
                785                 790                 795                 800
Arg Gly Met Ala Asn Ala Val Ile Leu Asp Pro Leu His Leu Gln Glu
                805                 810                 815

<210> SEQ ID NO 6
<211> LENGTH: 820
<212> TYPE: PRT
<213> ORGANISM: Oryza sativa

<400> SEQUENCE: 6

Met Met Leu Leu Ser Ser Tyr Ser Gly Gln Phe Pro Gly Val
1               5                   10                  15

Ser Pro Leu Gly Thr Arg Pro Lys Arg Ser Thr Val Val Pro Arg
                20                  25                  30

Pro Val Val Thr Arg Ala Gly Val Arg Asn Asn Leu Glu Val Val
                35                  40                  45

Gly Asn Ala Gly Thr Leu Gln Gly Met Asp Ile Asp Glu Leu Arg Val
        50                  55                  60

Ile Val Arg Lys Gln Leu Gln Gly Val Glu Leu Ser Pro Ser Ser Tyr
65                  70                  75                  80

Asp Thr Ala Trp Val Ala Met Val Pro Val Gln Gly Ser Arg Gln Ser
                85                  90                  95

Pro Cys Phe Pro Gln Cys Val Glu Trp Ile Leu Gln Asn Gln Gln Glu
                100                 105                 110

Asp Gly Ser Trp Gly His Ser Ala Gly Pro Ser Gly Glu Val Asn Lys
            115                 120                 125

Asp Ile Leu Leu Ser Thr Leu Ala Cys Val Leu Ala Leu Asn Ile Trp
        130                 135                 140

Asn Val Gly Gln Asp His Ile Arg Arg Gly Leu Ser Phe Ile Gly Arg
145                 150                 155                 160

Asn Phe Ser Val Ala Ile Asp Gly Gln Cys Ala Ala Pro Val Gly Phe
                165                 170                 175

Asn Ile Thr Phe Ser Gly Met Leu Arg Leu Ala Ile Gly Met Gly Leu
            180                 185                 190

Lys Phe Pro Val Met Glu Thr Asp Ile Asp Ser Ile Phe Arg Leu Arg
        195                 200                 205

Glu Val Glu Phe Glu Arg Asp Ala Gly Gly Thr Ala Ser Ala Arg Lys
        210                 215                 220

Ala Phe Met Ala Tyr Val Ser Glu Gly Leu Gly Arg Glu Gln Asp Trp
225                 230                 235                 240

Asp His Val Met Ala Tyr Gln Arg Lys Asn Gly Ser Leu Phe Asn Ser
                245                 250                 255

Pro Ser Thr Thr Ala Ala Ser Ala Ile His Ser Cys Asn Asp Arg Ala
            260                 265                 270

Leu Asp Tyr Leu Val Ser Leu Thr Ser Lys Leu Gly Gly Pro Val Pro
        275                 280                 285

Ala Ile Tyr Pro Asp Lys Val Tyr Ser Gln Leu Cys Met Val Asp Thr
        290                 295                 300

Leu Glu Lys Met Gly Ile Ser Ser Asp Phe Ala Cys Asp Ile Arg Asp
305                 310                 315                 320

Ile Leu Asp Met Thr Tyr Ser Cys Trp Met Gln Asp Glu Glu Ile
                325                 330                 335

Met Leu Asp Met Ala Thr Cys Ala Lys Ala Phe Arg Leu Leu Arg Met
            340                 345                 350
```

-continued

```
His Gly Tyr Asp Val Ser Ser Glu Gly Met Ala Arg Phe Ala Glu Arg
        355                 360                 365

Ser Ser Phe Asp Asp Ser Ile His Ala Tyr Leu Asn Asp Thr Lys Pro
370                 375                 380

Leu Leu Glu Leu Tyr Lys Ser Ser Gln Val His Phe Leu Glu Glu Asp
385                 390                 395                 400

Phe Ile Leu Glu Asn Ile Gly Ser Trp Ser Ala Lys Leu Leu Lys Gln
                405                 410                 415

Gln Leu Ser Phe Asn Lys Ile Ser Lys Ser Leu Met Pro Glu Val Glu
            420                 425                 430

Tyr Ala Leu Lys Tyr Pro Phe Tyr Ala Thr Val Glu Val Leu Glu His
        435                 440                 445

Lys Gly Asn Ile Glu Arg Phe Asn Val Asn Gly Phe Gln Arg Leu Lys
    450                 455                 460

Ser Gly Tyr Cys Gly Ser Gly Ala Asp Lys Glu Ile Leu Ala Leu Ala
465                 470                 475                 480

Val Asn Lys Phe His Tyr Ala Gln Ser Val Tyr Gln Gln Glu Leu Arg
                485                 490                 495

Tyr Leu Glu Ser Trp Val Ala Glu Phe Arg Leu Asp Glu Leu Lys Phe
            500                 505                 510

Ala Arg Val Ile Pro Leu Gln Ser Leu Leu Ser Ala Val Val Pro Leu
        515                 520                 525

Phe Pro Cys Glu Leu Ser Asp Ala Arg Ile Ala Trp Ser Gln Asn Ala
    530                 535                 540

Ile Leu Thr Ala Val Val Asp Asp Leu Phe Asp Gly Gly Gly Ser Met
545                 550                 555                 560

Glu Glu Met Leu Asn Leu Val Ala Leu Phe Asp Lys Trp Asp Asp His
                565                 570                 575

Gly Glu Ile Gly Phe Cys Ser Ser Asn Val Glu Ile Met Phe Asn Ala
            580                 585                 590

Val Tyr Asn Thr Thr Lys Arg Ile Gly Ala Lys Ala Ala Leu Val Gln
        595                 600                 605

Lys Arg Cys Val Ile Asp His Ile Ala Glu Gln Trp Gln Val Met Val
    610                 615                 620

Arg Ala Met Leu Thr Glu Ala Glu Trp Ala Ala Gly Lys His Ile Pro
625                 630                 635                 640

Ala Thr Met Gly Glu Tyr Met Ser Val Ala Glu Pro Ser Phe Ala Leu
                645                 650                 655

Gly Pro Ile Val Pro Val Ser Ala Tyr Leu Leu Gly Glu Glu Leu Pro
            660                 665                 670

Glu Glu Ala Val Arg Ser Pro Gln Tyr Gly Arg Leu Leu Gly Leu Ala
        675                 680                 685

Ser Ala Val Gly Arg Leu Leu Asn Asp Val Met Thr Tyr Glu Lys Glu
    690                 695                 700

Met Gly Thr Gly Lys Leu Asn Ser Val Val Leu Leu Gln Pro Leu Ala
705                 710                 715                 720

Ala Gly Gly Ala Ala Ser Arg Gly Gly Gly Ala Pro Ala Pro Ala
                725                 730                 735

Pro Ala Ser Val Glu Ala Ala Arg Ala Glu Val Arg Arg Ala Ile Gln
            740                 745                 750

Ala Ser Trp Arg Asp Leu His Gly Leu Val Phe Gly Ser Gly Gly Gly
        755                 760                 765

Ser Ser Ser Ser Ile Ile Pro Arg Pro Cys Arg Glu Val Phe Trp His
```

-continued

```
            770                 775                 780
Thr Gly Lys Val Ala Ser Val Phe Tyr Gln Glu Gly Asp Gly Tyr Ala
785                 790                 795                 800

Arg Lys Ala Met Arg Ser Met Ala Asn Ala Val Ile Leu Glu Pro Leu
                805                 810                 815

His Leu Gln Glu
            820

<210> SEQ ID NO 7
<211> LENGTH: 821
<212> TYPE: PRT
<213> ORGANISM: Oryza sativa

<400> SEQUENCE: 7

Met Ile Leu Pro Met Ser Ser Ala Cys Leu Gly Gln Phe Leu Arg Ala
1               5                   10                  15

Ser Pro Arg Gly Met Ile Glu Gln Phe Asn Arg Ala Pro Pro Leu Arg
                20                  25                  30

Val Ser Ile Arg Gly Ala Ala Gly Val Glu Lys Ser Leu Gly Leu Gly
            35                  40                  45

Arg Asn Ala Gly Ser Gln Gln Gly Met Gln Lys Asn Gln Leu Gln Asp
        50                  55                  60

Lys Ile Arg Lys Gln Leu Arg Glu Val Gln Leu Ser Pro Ser Ser Tyr
65                  70                  75                  80

Asp Thr Ala Trp Val Ala Met Val Pro Val Gln Gly Ser His Gln Thr
                85                  90                  95

Pro Arg Phe Pro Gln Cys Ile Glu Trp Ile Met Gln Asn Gln His Asp
                100                 105                 110

Asp Gly Ser Trp Gly Thr Asn Leu Pro Gly Ser Val Val Asn Lys Asp
            115                 120                 125

Ile Leu Leu Cys Thr Leu Ala Cys Val Val Ala Leu Lys Arg Trp Asn
        130                 135                 140

Thr Gly Arg Asp His Ile Ser Arg Gly Leu Asn Phe Ile Gly Lys Asn
145                 150                 155                 160

Phe Trp Val Ala Met Asp Glu Gln Thr Ile Ala Pro Val Gly Phe Asn
                165                 170                 175

Ile Thr Phe Ser Gly Leu Leu Asn Leu Ala Thr Gly Thr Gly Leu Glu
            180                 185                 190

Phe Pro Val Met Gln Thr Asp Ile Asp Gly Ile Phe His Met Arg Lys
        195                 200                 205

Ile Glu Leu Glu Arg Asp Ala Tyr Gly Thr Ala Ser Ser Arg Arg Ala
        210                 215                 220

Phe Met Ala Tyr Val Ser Glu Gly Leu Asp Ser Leu Gln Asp Trp Asp
225                 230                 235                 240

Gln Val Met Ala Tyr Gln Arg Lys Asn Arg Ser Ile Phe Asn Ser Pro
                245                 250                 255

Ser Ala Thr Ala Ala Thr Val Ile His Gly His Asn Asp Ser Ala Leu
            260                 265                 270

Cys Tyr Leu Asp Ser Leu Val Ser Lys Leu His Gly Pro Val Pro Val
        275                 280                 285

Met Tyr Pro Gln Asn Ala Tyr Ser Gln Leu Cys Met Val Asp Thr Leu
        290                 295                 300

Glu Lys Met Gly Ile Ser Asn Asn Phe Ser Cys Glu Ile Ser Asp Ile
305                 310                 315                 320
```

-continued

```
Leu Asp Met Ile Tyr Arg Leu Trp Ile His Asn Glu Glu Leu Met
            325                 330                 335

Leu Glu Met Gly Thr Cys Ala Met Ala Phe Arg Leu Leu Arg Met His
            340                 345                 350

Gly Tyr Asp Ile Ser Ser Asp Gly Met Ala Gln Phe Val Glu Gln Ser
            355                 360                 365

Ser Phe Asp Asp Ser Ile His Gly Tyr Leu Asn Asp Thr Lys Ala Leu
370                 375                 380

Leu Glu Leu Tyr Arg Ser Ser Gln Ile Arg Cys Leu Glu Asp Asp Leu
385                 390                 395                 400

Ile Leu Gln Asp Ile Gly Ser Trp Ser Ala Arg Val Leu Gln Glu Lys
                405                 410                 415

Ile Ser Ser Lys Met Thr His Lys Ser Glu Met Leu Gly Val Glu Tyr
            420                 425                 430

Ala Leu Lys Phe Pro Val Tyr Ala Thr Leu Glu Arg Leu Glu Gln Lys
            435                 440                 445

Arg Asn Ile Glu Gln Phe Lys Thr Lys Glu Gln Leu Lys Ile Glu Gly
            450                 455                 460

Phe Lys Leu Leu Lys Ser Gly Tyr Arg Gly Ala Ile Thr His Asp Glu
465                 470                 475                 480

Ile Leu Ala Leu Ala Val Asp Glu Phe His Ser Ser Gln Ser Val Tyr
                485                 490                 495

Gln Gln Glu Leu Gln Asp Leu Asn Ser Trp Val Ala His Thr Arg Leu
            500                 505                 510

Asp Glu Leu Lys Phe Ala Arg Leu Met Pro Ser Ile Thr Tyr Phe Ser
            515                 520                 525

Ala Ala Ala Thr Met Phe Pro Ser Glu Leu Ser Glu Ala Arg Ile Ala
530                 535                 540

Trp Thr Gln Asn Cys Ile Leu Thr Thr Val Asp Asp Phe Phe Asp
545                 550                 555                 560

Gly Asp Gly Ser Lys Glu Glu Met Glu Asn Leu Val Lys Leu Ile Lys
                565                 570                 575

Lys Trp Asp Gly His Gly Glu Ile Gly Phe Ser Ser Glu Cys Val Glu
            580                 585                 590

Ile Leu Phe Tyr Ala Ile Tyr Asn Thr Ser Lys Gln Ile Ala Glu Lys
            595                 600                 605

Ala Val Pro Leu Gln Lys Arg Asn Val Val Asp His Ile Ala Glu Ser
            610                 615                 620

Trp Trp Phe Thr Val Arg Gly Met Leu Thr Glu Ala Glu Trp Arg Met
625                 630                 635                 640

Asp Lys Tyr Val Pro Thr Thr Val Glu Glu Tyr Met Ser Ala Ala Val
                645                 650                 655

Asp Ser Phe Ala Val Gly Pro Ile Ile Thr Ser Ala Ala Leu Phe Val
            660                 665                 670

Gly Pro Glu Leu Ser Glu Glu Val Phe Arg Ser Glu Glu Tyr Ile His
            675                 680                 685

Leu Met Asn Leu Ala Asn Thr Ile Gly Arg Leu Leu Asn Asp Met Gln
            690                 695                 700

Thr Tyr Glu Lys Glu Ile Lys Met Gly Lys Val Asn Ser Ile Met Leu
705                 710                 715                 720

His Ala Leu Ser His Ser Gly Gly Arg Gly Ser Pro Glu Ala Ser
                725                 730                 735

Met Glu Glu Ala Lys Arg Glu Met Arg Arg Val Leu Gln Gly Ser Arg
```

```
                    740                 745                 750
Cys Asp Leu Leu Arg Leu Val Thr Arg Asp Gly Gly Val Val Pro Pro
            755                 760                 765

Pro Cys Arg Lys Leu Phe Trp Phe Met Ser Lys Val Leu His Phe Val
        770                 775                 780

Tyr Met Glu Lys Asp Gly Tyr Phe Thr Ala Asp Gly Met Met Ala Ser
785                 790                 795                 800

Ala Asn Ala Val Ile Leu Asp Pro Leu Gln Val Thr Leu Leu Pro Ser
                805                 810                 815

Gly Leu Gly Thr Leu
            820

<210> SEQ ID NO 8
<211> LENGTH: 821
<212> TYPE: PRT
<213> ORGANISM: Oryza sativa

<400> SEQUENCE: 8

Met Met Leu Pro Met Ser Ser Ala Cys Ser Gly Gly Gln Phe Pro Gly
1               5                   10                  15

Ala Ser Pro His Gly Ile Ile Pro Lys Gln Phe Ser Arg Ala Pro Arg
            20                  25                  30

Ile Arg Val Ser Ile Arg Gly Ala Ala Gly Val Glu Lys Ser Leu Gly
        35                  40                  45

Leu Gly Arg Asn Ala Gly Ser Gln Gln Gly Met His Lys Asn Glu Leu
    50                  55                  60

His Asp Lys Ile Arg Lys Gln Leu Arg Asp Val Gln Leu Gln Pro Ser
65                  70                  75                  80

Ser Tyr Asp Thr Ala Trp Val Ala Met Val Pro Val Gln Gly Ser His
                85                  90                  95

Gln Thr Pro Arg Phe Pro Gln Ser Ile Glu Trp Ile Leu Gln Asn Gln
            100                 105                 110

Tyr Asp Asp Gly Ser Trp Gly Thr Asn Leu Pro Gly Leu Val Val Asn
        115                 120                 125

Lys Asp Ile Leu Leu Cys Thr Leu Ala Cys Val Val Ala Leu Lys Arg
    130                 135                 140

Trp Asn Thr Gly Arg Asp His Ile Ser Arg Gly Pro Asn Phe Ile Gly
145                 150                 155                 160

Arg Asn Phe Ser Val Ala Met Asp Glu Gln Thr Val Ala Pro Val Gly
                165                 170                 175

Phe Asn Ile Thr Phe Ser Gly Leu Leu Ser Leu Ala Thr Arg Thr Gly
            180                 185                 190

Leu Glu Leu Pro Val Met Gln Thr Asp Ile Asp Gly Ile Ile His Ile
        195                 200                 205

Arg Lys Ile Glu Leu Glu Arg Asp Ala Tyr Gly Thr Ala Ser Ser Arg
    210                 215                 220

Arg Ala Phe Met Ala Tyr Val Ser Glu Gly Leu Gly Asn Leu Gln Asp
225                 230                 235                 240

Trp Asn Gln Val Met Ala Tyr Gln Arg Lys Asn Gly Ser Ile Phe Asn
                245                 250                 255

Ser Pro Ser Ala Thr Ala Ala Thr Ile Ile His Gly His Asn Tyr Ser
            260                 265                 270

Gly Leu Ala Tyr Leu Asp Phe Val Thr Ser Lys Phe Gly Gly Pro Val
        275                 280                 285
```

-continued

```
Pro Val Met Tyr Pro Gln Asn Ala Tyr Ser Gln Leu Cys Met Val Asp
    290                 295                 300

Thr Leu Glu Arg Met Gly Ile Ser Glu Ser Phe Ala Cys Glu Ile Ser
305                 310                 315                 320

Asp Ile Leu Asp Met Thr Tyr Arg Leu Trp Met His Asn Glu Glu Glu
                325                 330                 335

Leu Met Leu Asp Met Arg Thr Cys Ala Met Ala Phe Arg Leu Leu Arg
                340                 345                 350

Met His Gly Tyr Asp Ile Thr Ser Asp Gly Met Ala Gln Phe Val Glu
            355                 360                 365

Gln Ser Ser Phe Asp Asp Ser Ile His Gly Tyr Leu Asn Asp Thr Lys
370                 375                 380

Ala Leu Leu Glu Leu Tyr Lys Ser Ser Gln Leu Arg Cys Leu Glu Asp
385                 390                 395                 400

Asp Leu Ile Leu Glu Glu Ile Gly Ser Trp Ser Ala Arg Val Leu Leu
                405                 410                 415

Glu Lys Ile Ser Ser Lys Met Ile His Ile Ser Glu Leu Pro Glu Val
                420                 425                 430

Glu Tyr Ala Leu Lys Cys Pro Val Tyr Ala Ile Leu Glu Arg Leu Glu
            435                 440                 445

Gln Lys Arg Asn Ile Glu Gln Phe Lys Thr Lys Glu Gln Leu Lys Ile
450                 455                 460

Glu Gly Phe Lys Leu Leu Lys Ser Gly Tyr Arg Gly Val Ile Pro Asn
465                 470                 475                 480

Asp Glu Ile Leu Ala Leu Ala Val Asp Glu Phe His Ser Ser Gln Ser
                485                 490                 495

Val Tyr Gln Gln Glu Leu Gln Asp Leu Asn Ser Trp Val Ala His Thr
            500                 505                 510

Arg Leu Asp Glu Leu Lys Phe Ala Arg Leu Met Pro Ser Ile Thr Tyr
            515                 520                 525

Phe Ser Ala Ala Ala Val Leu Leu Pro Ser Glu Ser Ala Arg Ile Ala
530                 535                 540

Trp Thr Gln Asn Cys Ile Leu Thr Thr Thr Val Asp Asp Phe Phe Asp
545                 550                 555                 560

Gly Glu Gly Ser Lys Glu Glu Met Glu Asn Leu Val Lys Leu Ile Glu
                565                 570                 575

Lys Trp Asp Asp His Gly Glu Ile Gly Phe Ser Ser Glu Cys Val Glu
                580                 585                 590

Ile Leu Phe Tyr Ala Val Tyr Asn Thr Ser Lys Gln Ile Ala Glu Lys
            595                 600                 605

Ala Met Pro Leu Gln Lys Arg Asn Ala Val Asp His Ile Ala Glu Ser
            610                 615                 620

Trp Trp Phe Thr Val Arg Gly Met Leu Thr Glu Ala Glu Trp Arg Met
625                 630                 635                 640

Asp Lys Tyr Val Pro Thr Thr Val Glu Glu Tyr Met Ser Ala Ala Val
                645                 650                 655

Asp Ser Phe Ala Val Gly Pro Ile Ile Thr Ser Ala Ala Leu Phe Val
                660                 665                 670

Gly Pro Glu Leu Ser Glu Glu Val Phe Arg Ser Glu Glu Tyr Ile His
            675                 680                 685

Leu Met Asn Leu Ala Asn Thr Ile Gly Arg Leu Leu Asn Asp Met Gln
            690                 695                 700

Thr Tyr Glu Lys Glu Ile Lys Met Gly Lys Val Asn Ser Val Met Leu
```

```
705                 710                 715                 720
His Ala Leu Ser His Ser Gly Gly Arg Gly Ser Pro Glu Ala Ser
                725                 730                 735

Met Glu Glu Ala Lys Arg Glu Met Arg Arg Val Leu Gln Gly Cys Arg
            740                 745                 750

Phe Glu Leu Leu Gly Leu Val Thr Arg Asp Ala Gly Val Val Pro Pro
        755                 760                 765

Pro Cys Arg Lys Leu Phe Trp Leu Met Ser Lys Val Leu His Phe Val
    770                 775                 780

Tyr Met Glu Lys Asp Arg Tyr Phe Thr Ala Glu Gly Met Met Ala Ser
785                 790                 795                 800

Ala Asn Ala Val Ile Leu Asp Pro Leu Gln Val Thr Leu Pro Pro Ser
                805                 810                 815

Asp Ser Gly Thr Leu
                820

<210> SEQ ID NO 9
<211> LENGTH: 24
<212> TYPE: PRT
<213> ORGANISM: Oryza sativa

<400> SEQUENCE: 9

Cys Ala Cys Cys Ala Thr Gly Ala Thr Gly Cys Thr Gly Cys Thr Gly
1               5                   10                  15

Ala Gly Thr Thr Cys Cys Thr Cys
            20

<210> SEQ ID NO 10
<211> LENGTH: 24
<212> TYPE: PRT
<213> ORGANISM: Oryza sativa

<400> SEQUENCE: 10

Thr Thr Ala Cys Thr Cys Thr Thr Gly Cys Ala Gly Gly Thr Gly Cys
1               5                   10                  15

Ala Gly Thr Gly Gly Cys Thr Cys
            20
```